US009107615B2

United States Patent
Buckman

(10) Patent No.: US 9,107,615 B2
(45) Date of Patent: Aug. 18, 2015

(54) METHOD AND APPARATUS FOR BODY IMPACT PROTECTION

(75) Inventor: Robert F. Buckman, Elkton, MD (US)

(73) Assignee: Active Protective Technologies, Inc., Kennedyville, MD (US)

( * ) Notice: Subject to any disclaimer, the term of this patent is extended or adjusted under 35 U.S.C. 154(b) by 1042 days.

(21) Appl. No.: 12/428,780

(22) Filed: Apr. 23, 2009

(65) Prior Publication Data

US 2009/0254003 A1     Oct. 8, 2009

Related U.S. Application Data

(63) Continuation-in-part of application No. 11/640,783, filed on Dec. 18, 2006, now abandoned, which is a continuation-in-part of application No. 10/871,238, filed on Jun. 18, 2004, now Pat. No. 7,150,048, which (Continued)

(51) Int. Cl.
| | |
|---|---|
| *A61B 5/117* | (2006.01) |
| *A61B 5/103* | (2006.01) |
| *A61B 5/11* | (2006.01) |
| *A41D 13/018* | (2006.01) |

(52) U.S. Cl.
CPC ............. *A61B 5/1117* (2013.01); *A41D 13/018* (2013.01); *A61B 2562/0219* (2013.01)

(58) Field of Classification Search
CPC .................................................... A61B 5/1117
USPC ................ 600/595, 300, 301, 534; 601/33, 5; 434/29

See application file for complete search history.

(56) References Cited

U.S. PATENT DOCUMENTS

| | | | |
|---|---|---|---|
| 4,832,050 A * | 5/1989 | DiLullo | ......................... 600/595 |
| 4,977,623 A | 12/1990 | DeMarco | |
| 5,345,824 A | 9/1994 | Sherman et al. | |
| 5,362,098 A | 11/1994 | Guill | |

(Continued)

FOREIGN PATENT DOCUMENTS

| | | |
|---|---|---|
| DE | 40 03 683 A1 | 8/1991 |
| DE | 197 44 808 A1 | 4/1999 |

(Continued)

OTHER PUBLICATIONS

International Search Report dated Apr. 20, 2006 as received in related PCT Application No. PCT/US2005/012597, 2 pages.

(Continued)

*Primary Examiner* — Brian Szmal
(74) *Attorney, Agent, or Firm* — Foley & Lardner LLP

(57) ABSTRACT

A motion analysis system includes: at least one orientation sensor configured to detect three-dimensional torso motion over time, the at least one orientation sensor including: a multiaxial accelerometer configured to detect acceleration in at least three orthogonal directions, and a gyroscope; and a controller configured to receive data from the at least one orientation sensor, the controller programmed to process the data to: determine at least one of a state and a transition of the torso; identify normal parameters for the determined at least one of the state and transition; and determine whether motion of the torso is outside the normal parameters. The controller is configured to identify, in real-time, the occurrence of a fall in progress of an individual from at least one of a standing state, a standing-to-seated transition, and a seated-to-standing transition.

30 Claims, 12 Drawing Sheets

Related U.S. Application Data is a continuation-in-part of application No. 10/741,639, filed on Dec. 18, 2003, now Pat. No. 7,017,195.

(60) Provisional application No. 60/434,732, filed on Dec. 18, 2002.

(56) References Cited

U.S. PATENT DOCUMENTS

| | | | |
|---|---|---|---|
| 5,497,511 A | 3/1996 | Zade | |
| 5,500,952 A | 3/1996 | Keyes | |
| 5,539,935 A | 7/1996 | Rush, III | |
| 5,593,111 A | 1/1997 | Jackson et al. | |
| 5,846,086 A * | 12/1998 | Bizzi et al. | 434/247 |
| 5,919,149 A * | 7/1999 | Allum | 600/595 |
| 5,937,443 A | 8/1999 | Kageyama et al. | |
| 6,032,299 A | 3/2000 | Welsh | |
| 6,095,991 A | 8/2000 | Krausman et al. | |
| 6,119,516 A | 9/2000 | Hock | |
| 6,160,478 A | 12/2000 | Jacobsen et al. | |
| 6,166,639 A | 12/2000 | Pierce et al. | |
| 6,198,394 B1 | 3/2001 | Jacobsen et al. | |
| 6,201,476 B1 | 3/2001 | Depeursinge et al. | |
| 6,208,251 B1 | 3/2001 | Cadet et al. | |
| 6,270,386 B1 | 8/2001 | Visocekas | |
| 6,282,729 B1 | 9/2001 | Oikawa et al. | |
| 6,307,481 B1 | 10/2001 | Lehrman et al. | |
| 6,386,576 B1 | 5/2002 | Kamen et al. | |
| 6,418,564 B1 | 7/2002 | Sheridan | |
| 6,470,748 B1 | 10/2002 | Geen | |
| 6,570,503 B1 | 5/2003 | Ulert et al. | |
| 6,611,783 B2 | 8/2003 | Kelly et al. | |
| 6,700,499 B2 | 3/2004 | Kubo et al. | |
| 6,722,692 B2 | 4/2004 | Fukaya et al. | |
| 6,783,153 B2 | 8/2004 | Mattes | |
| 6,819,247 B2 | 11/2004 | Birnbach et al. | |
| 6,828,697 B2 | 12/2004 | Mattes | |
| 6,951,033 B2 | 10/2005 | Dainese | |
| 6,997,882 B1 * | 2/2006 | Parker et al. | 600/534 |
| 7,017,195 B2 | 3/2006 | Buckman et al. | |
| 7,141,026 B2 * | 11/2006 | Aminian et al. | 600/595 |
| 7,150,048 B2 | 12/2006 | Buckman | |
| 2001/0049840 A1 | 12/2001 | Atanasio | |
| 2002/0078484 A1 | 6/2002 | Ulert et al. | |
| 2002/0183657 A1 | 12/2002 | Socci et al. | |
| 2003/0197608 A1 | 10/2003 | Rudhard et al. | |
| 2003/0214408 A1 | 11/2003 | Grajales et al. | |
| 2004/0003455 A1 | 1/2004 | Davidson | |
| 2004/0039254 A1 * | 2/2004 | Stivoric et al. | 600/300 |
| 2004/0077975 A1 | 4/2004 | Zimmerman | |
| 2004/0111790 A1 | 6/2004 | Dainese | |
| 2005/0067816 A1 | 3/2005 | Buckman | |
| 2005/0195079 A1 | 9/2005 | Cohen | |
| 2006/0001545 A1 | 1/2006 | Wolf | |
| 2013/0312168 A1 | 11/2013 | Raanan | |

FOREIGN PATENT DOCUMENTS

| | | | |
|---|---|---|---|
| DE | 197 54 541 | | 6/1999 |
| DE | 198 38 022 C1 | | 5/2000 |
| EP | 1089215 A1 * | | 4/2001 |
| FR | 2778067 | | 5/1998 |
| GB | 2 312 369 A | | 10/1997 |
| JP | 08077497 A * | | 3/1996 |
| JP | 2000-051379 A | | 2/2000 |
| WO | WO-91/01658-AI | | 2/1991 |
| WO | WO-00/51453 A1 | | 9/2000 |

OTHER PUBLICATIONS

International Search Report dated Jan. 4, 2006 as received in related PCT Application No. PCT/US2004/043017, 1 page.

International Search Report dated Jun. 18, 2004 as received in corresponding PCT Application No. PCT/US2003/040588, 2 pages.

US Office Action dated Apr. 15, 2005 as received in corresponding U.S. Appl. No. 10/741,639.

US Office Action dated Dec. 23, 2008 as received in corresponding U.S. Appl. No. 11/640,783.

US Office Action dated Feb. 8, 2006 as received in corresponding U.S. Appl. No. 10/871,238.

* cited by examiner

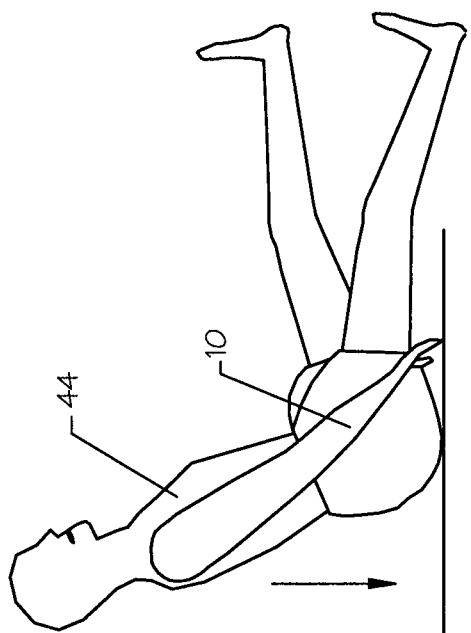
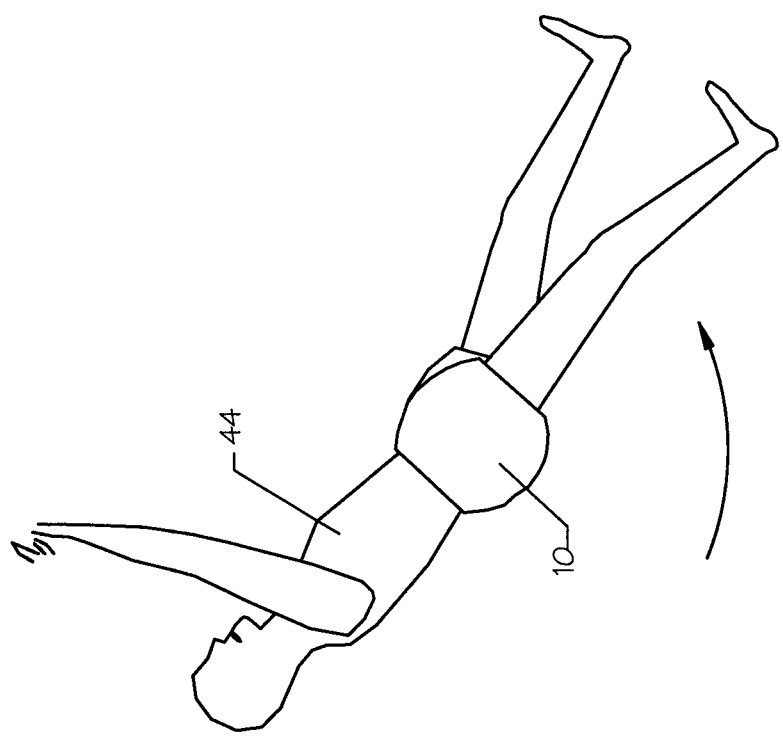
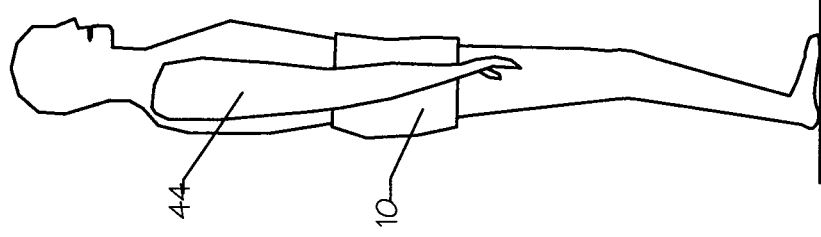

METHOD AND APPARATUS FOR BODY IMPACT PROTECTION

This application is a continuation-in-part of U.S. application Ser. No. 11/640,783 filed Dec. 18, 2006, now abandoned which is a continuation-in-part of U.S. application Ser. No. 10/871,238 filed Jun. 18, 2004 now U.S. Pat. No. 7,150,048, which is a continuation-in-part of U.S. application Ser. No. 10/741,639 filed Dec. 18, 2003 now U.S. Pat. No. 7,017,195, which in turn claims priority benefit under 35 USC §119(e) from U.S. Provisional Application 60/434,732 filed Dec. 18, 2002.

FIELD OF THE INVENTIONS

The inventions described below relate to devices and methods for protecting the body from injuries that result from impacts and falls, especially in elderly persons via the use of devices to detect a fall in progress and deploy protective measures.

BACKGROUND OF THE INVENTIONS

Two of the common effects of aging are the onset of osteoporosis or other degenerative bone disease and the impairment of balance so that falls are frequent and often the cause of serious injuries in the elderly. In particular, fracture of the hip and pelvis are extremely common in older people. Such fractures can occur when a stationary or walking person falls when standing or sitting, if a person falls out of bed, or if a person falls down steps. Additionally, serious impacts may occur if a person is involved in a vehicular accident where velocities are considerably higher.

Persons who experience a hip or pelvic fracture often require hip-nailing or replacement surgery. While such repairs are often quite satisfactory, they are expensive and cause a significant financial drain on the health care system. In addition, patients who experience a hip fracture often experience compromised physiological function as a result of the fracture. In some cases, a patient may die as a result of the hip fracture and its sequelae. Among survivors, a fracture to the hip may also start a downward spiral in health that ultimately may lead to loss of independence and necessitating admission to a nursing home. Although fracture of the hip or pelvis is an injury characteristic and common to falling, many other injuries, especially of the brain, cervical spine, arms, and ribs are also common. Falls are, thus, a major cause of mortality and morbidity.

There are no satisfactory devices available today to protect persons from falls or other impacts in such a way that bone fracture may be prevented during every day activities. While people might wear body armor, helmets and the like, such armor and helmets would be too heavy, bulky, unattractive, and cumbersome for people to be willing to wear on a regular basis.

New devices, systems, and methods are needed to recognize when an individual is falling in order to protect them from the fall or other impacts that might lead to bone fracture and other serious injuries. Such devices are particularly important in the elderly where bone structure and balance may be compromised.

SUMMARY

This invention relates to active devices, fall-sensors and personal airbags used in garments and clothing designed to protect an individual from an impact injury, especially those due to accidental falls.

The invention is an active protective system or active protection garment (APG) that includes detection, activation, and protection mechanisms. The protection mechanism is automatically deployed via an air bag inflator when sensors detect the accelerations, directions or rotations associated with the early phases of an accidental fall. The active protection system comprises a garment that is worn by a person or animal requiring protection. The garment may be, depending on the part of the body to be protected, a vest, coat, hat, helmet, pants, shorts, underpants, shirt, undershirt, jumpsuit, shoes, socks, scarf, or other clothing. The system or garment may further comprise elements added to conventional articles of clothing. The garment, or added elements, comprises structures, analogous to an airbag, that are capable of inflating or expanding to provide protection to the wearer. The garment, or added elements, further includes sensors, or a plurality of sensors, that detect the orientation of the body or torso, the acceleration, the velocity, the rotation and the position of the garment or person or the forces acting on the garment itself. The APG further comprises a logic controller that is capable of activating the air bag inflator should certain criteria be met or fall outside of an acceptable range. The logic controller is capable of distinguishing from a fall another normal daily activities that can be mistakenly interpreted as a fall. The APG logic controller interprets electromagnetic inputs from the linked gyroscopic, position, velocity, or accelerometer devices. The air bag inflator is activated by the logic controller, deploying airbags or pockets on or in the garment that are rapidly and automatically expanded to provide energy dissipative or distributive padding to those areas of the body, of the person or animal wearing the garment, requiring protection from the fall or other impact. The garment further comprises an exterior surface that is capable of withstanding the local forces that might be experienced by the garment, including tension, compression, shear, abrasion, puncture, and the like.

The active protection garment for an elderly person, can be a pair of shorts, or briefs, that are worn about the waist and extend downward to cover and provide active protection for the hips. The APG components can be built into baffles in the underwear or outerwear. These Upshots can be underwear or undershirts so that a more stylish garment may be worn overtop of the functional underwear. The Upshots may comprise part of a garment that is worn as the outer layer of clothing. The Upshots may have an elastic waistband that is easy to take on and take off. The leg openings may be close fitting, again for ease of the user. The Upshots can be fabricated from two separate fabric layers of non-gas-porous material, such as, but not limited to, rip-stop nylon, polyester, Kevlar, polyolefin, ePTFE, and the like. The separate layers can be further subdivided into pockets or chambers that are isolated from each other. The fabric layers of the APG comprise regions of porosity to allow for breathability.

When the sensors detect the conditions of a fall in progress as evidenced by acceleration, distance, velocity, direction, discoordination, or a combination of parameters, etc., the controller sends a signal, by hardwire or electromagnetic radiation (e.g. radio waves, infra-red, microwave, etc.), to the logic controller. The logic controller sends an electrical or electromagnetic signal to the airbag inflator letting $CO_2$ (or other) gas move from the canister through the conduits to the subdivided chambers of the APG shorts. Alternatively, the logic controller may send the electromagnetic signal to the valve, causing it to open. The subdivided chambers or airbags inflate to a pre-specified pressure. The pressurized chambers provide additional padding around the hips to prevent bone fracture when the individual hits the ground or other surface. The multiple isolated chambers prevent unwanted redistribution of the pressure away from the impact site on the APG shorts. The APG is tailored to the anatomy of the site requiring protection. The garment may also be tailored to accept airbag elements placed in pockets designed for this purpose.

The biomechanics or ballistics of falling from standing height requires that the system react to deploy within 0.5 seconds or less. For example, in a directly vertical fall from standing, for a 5-foot tall person, the hips drop 2.5 feet, at the 32-ft/sec$^2$ acceleration due to gravity, before they hit ground in approximately 0.28 seconds. Other types of falls, including slips while walking, tripping, falling forward, or falling backward, may involve changes in verticality from the loss of balance to the impact. If the sensors detect an orientation, distance, acceleration, or direction that moves beyond programmed limits from vertical to horizontal too quickly or where the gravitational force on the sensors falls below programmed limits, the APG shorts are activated. Activation involves deployment or inflation of the airbags. Activation, deployment of the airbag or other barrier, must be complete within a fraction of a second from the start time of the fall. The wearer might not want to wear the APG shorts on a roller coaster or other ride where such forces might occur and cause a false positive activation. Alternatively, a manual disarm switch may be provided for use in circumstances where the APG might deploy inappropriately or unnecessarily.

The invention also relates to a motion analysis system that can detect normal motions associated with various different human activities. The activities can include the normal acts of walking, sitting and lying down, which can be distinguished from falls. Specifically, normal activities of an elderly person can be distinguished from falls in order to help prevent injury.

The system includes sensors mounted on an individual's torso. A preprogrammed logic circuit determines the orientation of the torso and interprets the trajectory of observed motions relative to the torso orientation. Multi-function sensors, mounted on the torso of an individual, are used to sense the orientation of the torso and determine its motions as a geometric solid in three-dimensional space. Through the use of novel algorithms and rules, it can be determined if the torso is moving along trajectories that are, or are not, characteristic of programmed normal activities. The direction of the motions of the torso, rather than just the magnitude of acceleration, is used to distinguish falls from normal activities.

The system includes a logic controller that is capable of distinguishing a fall from another normal daily activities that can be mistakenly interpreted as a fall. The logic controller interprets electromagnetic inputs from the linked sensors, gyroscopic, position, velocity, or accelerometer devices.

The algorithm for detection of an accidental fall could use any number of parameters to trigger inflation of the APG such as: 1) A rotation rate between sensors on the waistband or torso and at the bottom of the leg exceeding 45 degrees in 0.1 seconds would trigger activation of the inflation mechanism; 2) a nearly weightless condition for a period of 0.1 seconds would also trigger an inflation; or 3) lateral and vertical accelerations meeting certain parameters with respect to each other and with respect to normal values would trigger the inflation. Additional algorithms include velocity measurements where the vertical velocity is becoming increasingly negative (increasingly fast approaching the ground) and the horizontal velocity is increasingly positive. This scenario correlated with a vertical velocity in magnitude greater than negative 1 meter per second are strong indicators of a fall in progress and are distinguished from normal conditions such as sitting down, getting into a bathtub, putting on shoes, walking, etc. Another approach is to trigger the device based on velocity slope reversal such as when the vertical velocity falls outside a set range such as 1 meter per second and moves from positive to negative in a short period of time (usually less than 0.25 seconds).

Alternatively, a distance sensor using, for example ultrasound, microwave, radar, sonar, or infrared distance measurement would continuously ping the environment to determine the distance to objects such as the floor, a chair, etc. Derivatives of the distance, specifically by differentiating over time, would be continuously calculated to determine velocities and derivatives of the velocity would determine accelerations. Such distance sensors with their first order and time-differentiated measurements are used to calculate the presence of a fall in progress. Basic accelerometers can provide much of the needed information. Here, the nearly weightless condition would be, for example, an acceleration of less than ½G, or 16 ft/sec$^2$. The inflation period occurs in 0.1 second or less. A lateral acceleration exceeding 0.5 g for a specific period of time would also trigger deployment or activation. The distance measuring system operates in conjunction with one or more accelerometers and can provide information relating to the occurrence of an actual fall in progress.

The relative position of the accelerometer devices may be tracked by the system. This can be achieved by keeping a record of location over time using a look-back algorithm. However stacking errors will render such a system difficult to accomplish. One possible method or system is to periodically re-calibrate position relative to an absolute location, position, or level plane. The plane is preferably defined in the right-left direction, anterior-posterior direction north-south direction, and up-down direction. The re-calibration is significant to determine, for example when a wearer is standing up versus lying down or when a wearer is standing versus falling.

The sensors may comprise a plurality of accelerometers coupled to a plurality of primary position sensors. The accelerometers and position sensors are distributed over the person to be protected. One or more or all of these devices can be implantable but could also be made part of a garment or jewelry. Using transponder technology or RF receiver-transmitter technology, sensors without power supplies may be distributed around the patient. Energy is transmitted from a power source to transponders that are distributed at pre-determined locations on the body. The power is used to operate accelerometers and position sensors in sensor modules. The system can comprise a level that is affixed, removably or permanently, to the patient. The transponders periodically update their relative positions relative to each other and relative to level as determined by a leveling system. An external leveling system, on a walker, bed, or chair for example is suitable for providing the reference points needed to calibrate the system.

The APG can utilize a plurality of accelerometers to determine the status of the wearer. An example of an accelerometer suitable for such purpose is disclosed in U.S. Pat. No. 5,345,824 to Sherman et al, the entire specification of which is incorporated herein by reference. The accelerometers should function in at least two orthogonal planes and at least two, and preferably three or more, such multidirectional accelerometers are used providing three orthogonal directions of acceleration detection and analysis. Each accelerometer measures along three orthogonal axes. Thus, velocity, distance, and acceleration are measured along with rotation rates, distances, and accelerations. Outputs from the accelerometers are monitored and algorithms including integration and differentiation, are performed to determine velocity and distance. Velocities in both the forward and negative direction are determined by calculating the integral of the acceleration data over time and position information is obtainable by further taking the integral of the velocity data over time. Accelerometers such as those manufactured by ST Microelectronics, Analog Devices, or Motorola are appropriate for this application. An accelerometer with a range of ±2 g is acceptable for this application. An accelerometer with a range of ±1 g is also acceptable and accelerometers with larger ranges might also work although they would have reduced resolution in the critical ±1 g range where most fall data occurs. A two-direction accelerometer is advantageous over a one-direction accelerometer and a three-direction accelerometer is most advantageous. Two such multi-direction accelerometers can be used and their outputs correlated to determine the event of a fall in progress.

The logic circuitry or computer onboard the APG will necessarily run a sophisticated program to continuously monitor sensor outputs, integrate or differentiate as necessary, and develop motion information. The system needs to integrate or differentiate the data, continuously track motion, and use a look-back function for periods on the order of 1 second to 10 minutes. The look-back function should last between 10 seconds and 60 seconds. During the look back period, the computer will evaluate motion and determine whether a fall is in progress as dictated by pre-set conditions or string of conditions or rules. The measured motions are continuously evaluated against the rules to determine whether or not a fall is in progress. Significant computational power including processor speeds and memory are required for such computations to be performed. For example, a 100 mHz or higher clock speed in the processor and memory of 128 megabyte or more is preferred. Sensing rates of 1,000 measurements per second for three accelerometers along three axes implies 9,000 measurements per second. Sixty seconds of data will require 60 times 9,000 or 540,000 measurements. The memory will require approximately 1 megabyte to hold 540,000 16-bit words. To obtain velocity and distance, another 2 megabyte of 16 bit words are required. Computational storage may require an additional 32 megabytes of memory. Therefore a system with approximately 48 to 64 megabytes of memory should be more than sufficient.

Alternatively, the sensor outputs can be recalibrated at predetermined intervals based on the user activity or position of the body, without any reference to any external standard. New programs can triggered within the logic circuit based upon the state of the monitored user or on the observation by the logic controller of a transition between predetermined states. Parameters can be programmed for allowable motions in each direction for each predetermined body-state and transition.

The logic circuitry can be programmed with algorithm rules that define the motion signatures for the major activity states as well as the transition between the states. Additionally, other rules define the significant departures from the normal motions that indicate falls or the harbingers of falls. The three normal human activity states are defined as the state of standing or walking, the state of being seated and the state of recumbency. The normal transition states are: 1) from the standing state to the seated state; 2) from the seated state to the standing state; 3) from the seated state to the recumbent state; and 4) from the recumbent state to the seated state. The recognition of these transition sequences establishes the body-states for use by the logic controller. The logic controller is programmed to recognize the patterns of normal translations between states and how these differ from fall motions. The individual state and transition programs will recognize normal and abnormal patterns of motion for the state or the transition. The program for each state is triggered either by the end of the transition to that state or by the observation of signature motion for that state. The transitional programs are triggered by the observation of signature torso motions that indicate the possibility of a transition between one state and another. Observed torso motions will be referenced to the body state or transition as being normal or abnormal. Parameters are programmed for allowable motions in each direction for each body-state and transition. This is performed by either a neutral network or a statistical program of pattern matching. The range of normal trajectories during each of the transitions is established. Downward motions of the torso not corresponding to programmed parameters for a given transition because of abnormal sequence, acceleration or trajectory is recognized as falls. The delineation of the normal motion signatures for the standing/walking state, the seated state and the recumbent state and for the transitions between states is programmed during a training phase.

Alternatively, in the APG system, sensors can be located in or on the patient. The sensors are transponders or RF ID type devices. A transmitter transmits wireless signals at a certain frequency. The RF ID transponder receives the information and re-transmits at a new frequency. A sensor or sensors mounted on the patient determine the beat frequency between the transmitting and receiving transducers and calculates relative motion between the two transducers using Doppler shift methodology. This method can be used to determine the distance between a plurality of transducers affixed, removably or permanently, to the patient. The RF ID device, can also use microwave, RF, ultrasound, sound, or simple electrical signals transmittable through body tissue, and the like.

The APG system comprises algorithms to understand whether the person is walking, standing, sitting, lying down, or the like. These algorithms are used to supplement and real-time and/or look-back motion data to determine whether a fall-in-progress is occurring.

The APG can comprise rotational acceleration sensors such as the type manufactured by ST Microelectronics. Such rotational acceleration sensors are capable of measuring rotational acceleration. The information can be derived over time to obtain rotational velocity and derived again over time to obtain rotation distance or angle. Such rotational acceleration information can be used alone or in conjunction with other accelerometers or distance sensors to detect a fall in progress. A rotational accelerometer system has the potential to eliminate the need for one or more linear accelerometers in the entire system, thus providing for more simplicity and cost-savings.

The APG can also comprise one or more gyroscopes of the type disclosed in U.S. Pat. No. 6,470,748 to Geen, the entire specification of which is incorporated herein by reference. The gyroscopes can be used alone, or in conjunction with the accelerometers.

A plurality of accelerometers or other sensors can be distributed on the patient by either implantation, or by adhesive attachment to the patient via a patch or patches. The implantation or adhesive attachment to the patient provides reliable, repeatable location for the sensors that can be relied on to generate data that is useable by the logic controller to detect a fall in progress. Sensors that are not well affixed to the patient, such as those affixed to garments or jewelry, will be less well attached to the patient so positioning is less accurate and more subject to errors in measurement or inappropriate locating by the patient. The logic circuitry generally requires exacting knowledge of the positioning of the sensors to determine the interrelationship between the measurements that are taken. The logic circuitry integrates or differentiates the data from the plurality of sensors, preferably three or more three-dimensional sensors that can measure motion in three directions and three axes of rotation, relative to time. Rotation rates of accelerometers requires that acceleration data be derived to determine velocity and that the moment arm between the two sensors be known with substantial precision.

BRIEF DESCRIPTION OF THE DRAWINGS

FIG. 5A illustrates a side view of a pair of APG shorts on a standing individual;

FIG. 5B illustrates a pair of APG shorts, which have activated because they are being worn by an individual who has begun falling;

FIG. 5C illustrates a pair of APG shorts being worn by an individual who has fallen and whose hip has struck the ground;

DETAILED DESCRIPTION OF THE INVENTIONS

Figure 1A:
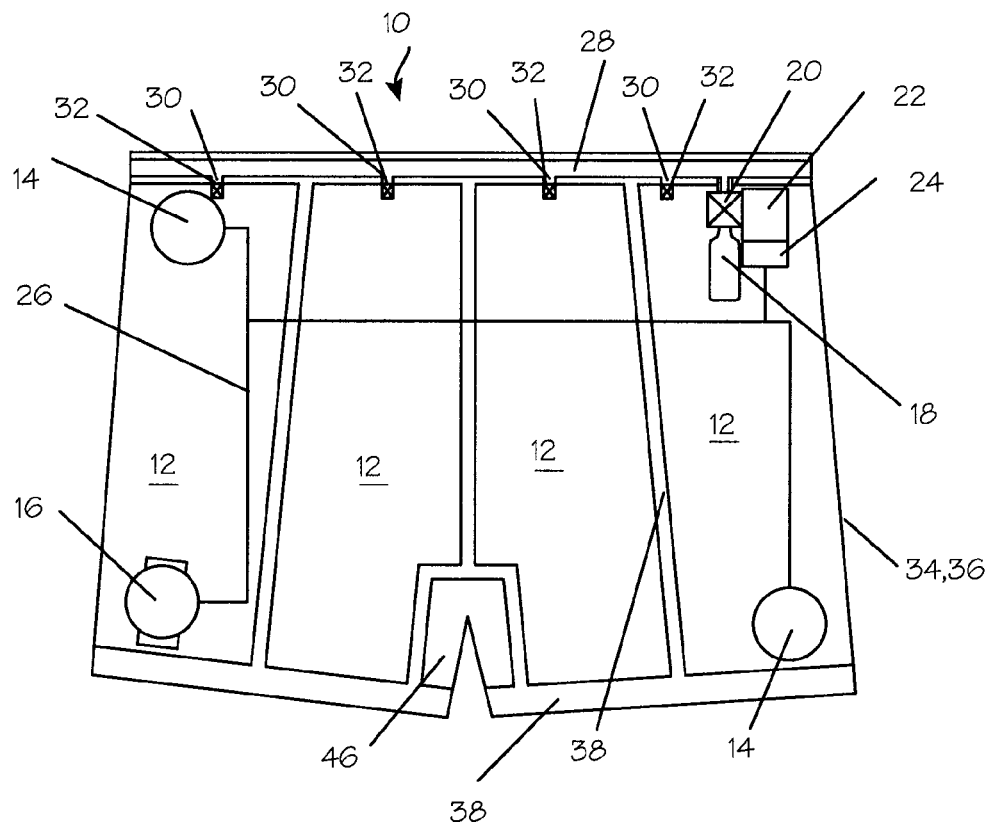
FIG. 1A illustrates a pair of deflated APG shorts.

FIG. 1A illustrates pair of deflated APG shorts 10. The APG shorts 10 comprise a plurality of chambers 12, a plurality of accelerometers 14, one or more optional gyroscope 16, a high pressure or compressed source of gas 18, a logic controller 22, a battery 24, an electrical bus 26, a manifold 28, a plurality of chamber inlet ports 30, and a plurality of one-way valves 32. The APG shorts can optionally have an actuator valve 20. The chambers 12 can further comprise two layers of gas impermeable wall 34 and 36, a plurality of seals 38 and one or more non-inflatable regions 46.

The chambers 12 are isolated regions within the APG shorts 10 that cushion the impact between the wearer and the object being hit by the wearer. The chambers 12 are connected to the high pressure or compressed gas source 18 by a manifold 28. A valve 20 may be contained to control and enable the gas flow from the compressed gas source 18 to the manifold 28. The entry to each chamber 12 is a chamber inlet port 30. Each chamber inlet port 30 may be connected to the manifold 28 by a one-way valve 32. The valve 20 is opened or closed by the logic controller 22, which is further powered by a power supply 24. Inputs to the logic controller 22 are electrically connected to a plurality of accelerometers 14 and/or a plurality of gyroscopes 16 by an electrical bus 26. The APG short also comprise a plurality of non-inflatable regions 46. All components are affixed to the APG shorts 10.

The chambers 12 can comprise cornstarch, talc or other dry lubricant to prevent blocking or wall adherence that could prevent proper inflation when desired.

The high pressure or compressed gas source 18 can be a canister of gas such as, but not limited to, carbon dioxide, nitrous oxide, nitrogen, argon, or the like. The high pressure or compressed gas source 18 may also be a pyrotechnic device or a catalytic device that, once activated by the air bag inflator, generates a gas such as nitrogen, carbon dioxide or other non-flammable material, that expands under great pressure to fill the manifold 28 and the chambers 12. A typical solid-state gas source comprises sodium azide ($NaN_3$) with a potassium nitrate ($KNO_3$) oxidizer encapsulated within a filter and containment chamber with holes through which gas can escape. The device further comprises an electrical air bag inflator that causes activation when the proper electrical signal is applied to the inflator. Typical devices of this type use 12 Volts DC and 750 milliamps to activate the inflator although lower energy inflators are possible and desirable. Such gas sources 18 are capable of fully outgassing beginning around 5 milliseconds from the presence of the electrical signal in the inflator and completely outgassing in times as short as 40 milliseconds or less. Longer outgassing times, up to 100 or 200 milliseconds, may be appropriate for the application of the Active Protective Garment. Very fast outgassing devices have uses in systems where the fall is detected in its terminal stages or even after impact when a velocity reversal occurs. Extremely fast inflation at that point may still distribute forces and prevent injury to the wearer.

When the Active Protective Garment contains a valve, 20 the valve is activated either by motor or explosively operated such that once a triggering signal is received from the logic controller 22, the valve opens within less than 0.05 seconds and preferably within less than 0.01 seconds. The high-speed opening mechanism of the valve 20 is either fusible or motor-driven. The valve 20 optionally comprises a pressure regulator to ensure that the proper pressure is applied to the manifold 28 and, subsequently, the chambers 12. When the valve is not present, the air bag inflator deploys within these same time limits.

The one-way valves 32 are passive valves that permit gas to enter the chamber inlet ports 30 but not to escape in a retrograde direction. Valves of this type include, but are not limited to, duck bill valves.

One or more non-inflatable regions 46 are located in areas that normally would not require protection and which, if explosively inflated might cause damage or discomfort to the person wearing the APG shorts 10. Such areas where a non-inflatable region 46 is appropriate include the crotch area. Selective areas of non-activation such as the non-inflatable region 46 are preferably in areas that would not normally receive an impact load during a fall.

The electrical bus 26 includes all electrical wiring between the sensors, including the gyroscopes 16 and the accelerometers 14 and the logic controller 22. The electrical bus 26 is also comprised within the logic controller 22 interconnecting all components electrically. The electrical bus 26 also connects the logic controller 22 and the air bag inflator or the valve 20, thus sending a signal to open at the appropriate time.

Figure 1B:
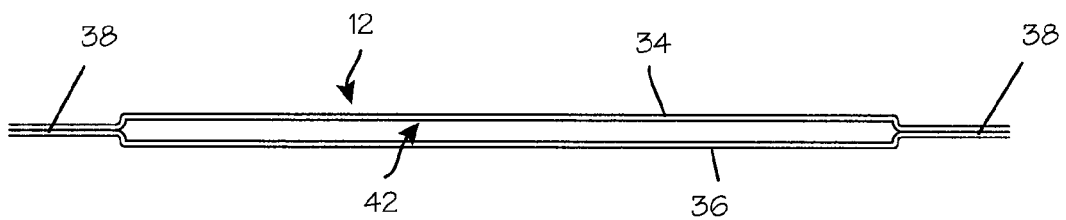
FIG. 1B illustrates a cross-sectional view of one of the deflated chambers of the APG shorts.

FIG. 1B illustrates a cross-sectional view of a chamber 12 of the deflated APG shorts 10. The chamber 12 further comprises an inner wall 34 and an outer wall 36, seals 38, and an interior volume or space 42. Suitable materials for the inner wall 34 and the outer wall 36 include, but are not limited to, polyester (PET), polyimide, polyurethane, polytetrafluoroethylene (PTFE), nylon, Dacron, Kevlar, copolymers of the aforementioned, rip-stop nylon, cotton, and the like. The inner wall 34 and the outer wall 36 may be of different materials or they may be of the same materials. The material is preferably woven to maximize strength although knitting or other fabric forming processes are also acceptable. Strengthening fibers fabricated from Kevlar or polyester, for example, may be used in conjunction with weaker materials to form a barrier cloth that is impermeable to gas but also has reinforcing strands. Impermeability may be achieved by coating a woven or knitted fabric with membranous materials such as polyurethane or PTFE. Alternatively, the entire wall 34 and 36 can be fabricated from polymeric sheet that is not woven or reinforced but is homogeneous.

Figure 2A:
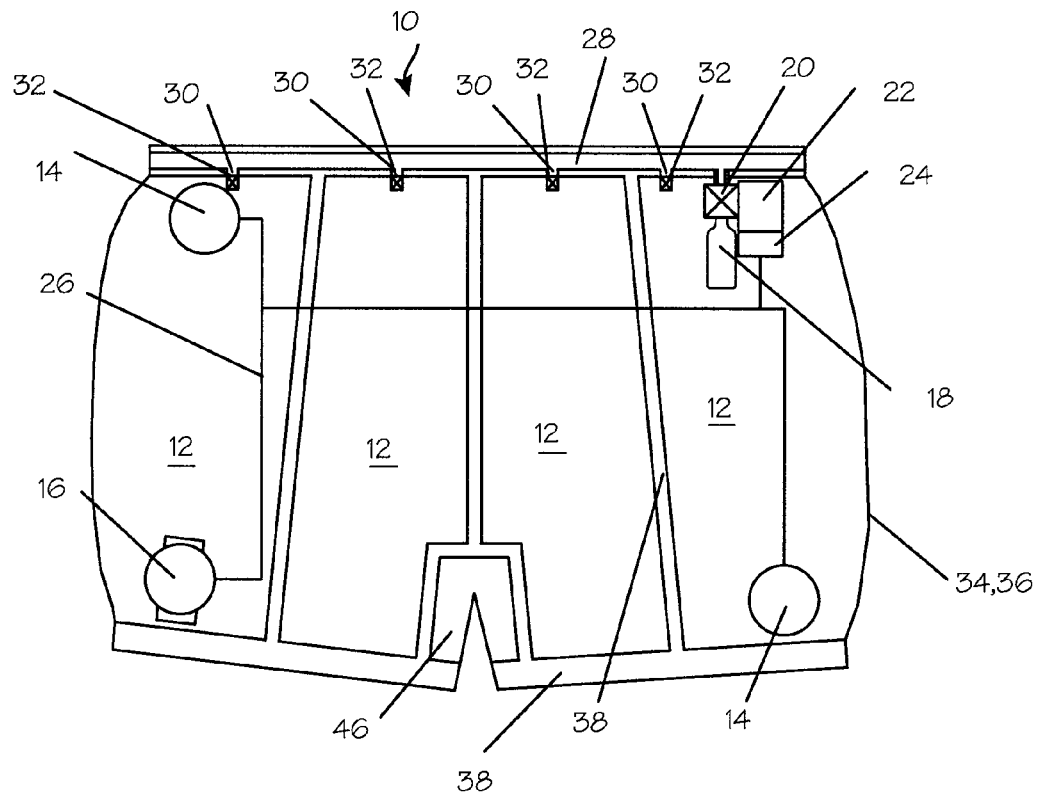
FIG. 2A illustrates a pair of APG shorts following activation.

FIG. 2A illustrates a pair of APG shorts 10 following activation. Referring to FIGS. 2A and 1B, the plurality of chambers 12 have become filled with pressurized gas and bulge outward to form a padded structure. Any amount of pressure generated within the interior volume 42 of the chambers 12 will provide some protection for the wearer, although sufficient pressure to prevent collapse of the exterior wall 36 against the interior wall 34 is preferable. For example, a 200-pound person resting on a 12-inch by 12-inch area or 1-foot square would require 1.39-pounds per square inch (PSI) internal pressure to support the weight. The same two hundred pound person falling from 2.5 feet would have an impact velocity of 8-ft/sec and exert a force greater than 200-lb due to their momentum. If they decelerated to a stop in 0.05 seconds when they hit the ground, the net force would equal 1000 pounds. Thus, the APG shorts require at least 6.94-pounds per square inch (PSI) to cushion the fall over a 1-square foot (144 square inch) area, under this scenario.

Figure 2B:
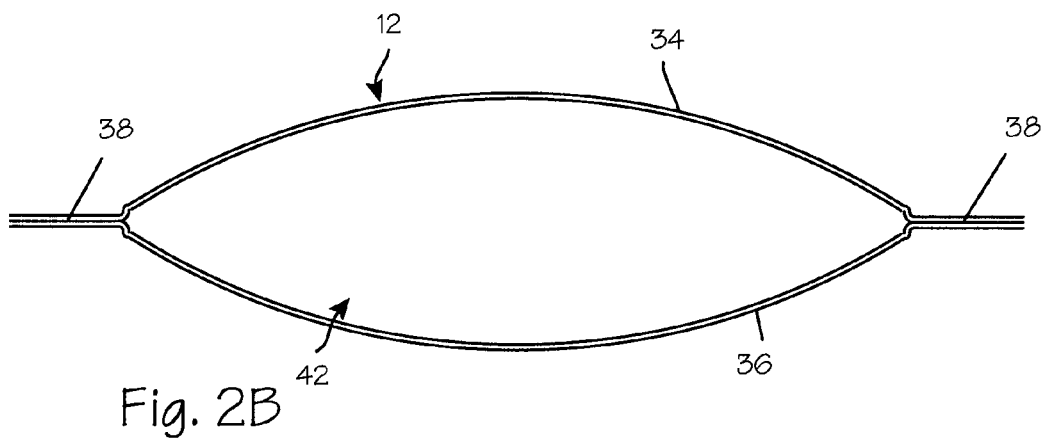
FIG. 2B illustrates a cross-sectional view of a chamber of the APG shorts following activation.

FIG. 2B illustrates a cross-sectional view of a chamber 12 of the APG shorts 10 following activation. The chamber 12 further comprises the inner layer 34 and the outer layer 36, a plurality of seals 38 and an inner volume 42. The chamber 12 has become inflated with pressurized gas and forms a padded structure to protect the wearer. The internal pressure within the internal volume 42 of the chamber 12 is sufficient to prevent collapse of the inner volume 42 between the inner layer 34 and the outer layer 36 of the chamber 12. The width of the seals 38 is sufficient to provide a strong bond so that the two layers 34 and 36 do not become separated by the tensile forces created by the pressurized internal volume 42. The width of the seals 38 is not so wide that the person wearing the APG shorts 10 would be unprotected if they fell on the seal 38. The seal 38 can be a heat seal created by compression of the two fabric layers 34 and 36 at specified temperatures, pressures and times such as to form a strong weld between the two layers 34 and 36 of material. Alternatively, each chamber 12 can be separate from the next and the separation wall does not comprise a seal 38.

Figure 3A:
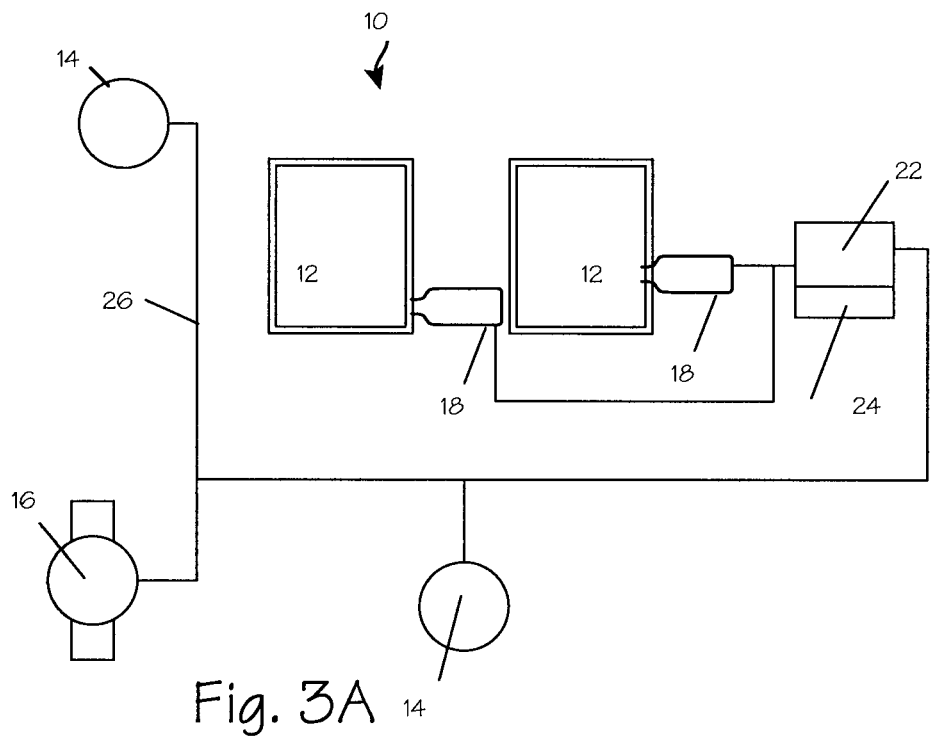
FIG. 3A illustrates a block diagram of the components of a pair of the APG shorts.

FIG. 3A illustrates a block diagram of the systems comprising the APG shorts. The APG shorts comprise a plurality of cushioning chambers 12, one or more accelerometers 14, one or more gyroscopes 16, a high pressure or compressed gas source 18, a logic controller 22, and a power supply 24.

The logic controller 22 is a computer and controls all aspects of function of the device from acquiring information from the gyroscopes 16 and the accelerometers 14 to determining whether an actuation condition exists to the airbag inflator (not shown) to inflate the chambers 12 to providing notification of the status of the power supply 24 or controller 22 malfunction. The software (not shown) controls the function of the logic controller 22.

The power supply 24 can be a battery system powered by chemistries such as, but not limited to, lithium ion, nickel metal hydride, nickel cadmium, alkaline, lead-acid, and the like. The power supply 24 provides electrical power at the correct voltage and current to the electrical components of the APG shorts 10. The power supply 24, optionally further comprises a connection to either 110 VAC or 240 VAC power and serves as a charger for the battery, if appropriate.

The accelerometers 14 can be strain gauge devices that suspend a weight on one or more strain gauges. The strain gauges operate within a Wheatstone bridge signal conditioning circuit to cause voltage or current changes in the circuit proportional to the stress on the accelerometer 14. Strains and stresses in multiple directions may be measured using a plurality of these strain gauges. The strain gauge, signal conditioners, amplifiers and other required components may be comprised within a single monolithic structure for manufacturability, small size, low cost, and reliability. The accelerometers 14 may be distance or position sensors such as those employing ultrasonic acoustic waves, radar, microwave, infrared, or other methods to determine distance between the sensor and the ground or other object. Differentiation of the signal provides velocity information and further differentiation provides acceleration information. The velocity, distance, and acceleration information can be correlated to signal a fall in progress and activate the APG shorts 10.

The accelerometer 14 can be an ST Microelectronics LIS3L02. This device is available as either an analog or digital output device capable of measuring acceleration along three orthogonal axes. It is a micro-electromechanical system (MEMS) based chip that requires support circuitry including power supply, timing, and output circuitry.

The gyroscope 16 may be a ball or sphere suspended concentrically within a sphere. The outer sphere is affixed permanently to the APG shorts 10. The inner sphere is magnetically suspended within the outer sphere. The inner sphere is weighted so that slow motions of the outer sphere move the inner sphere in a 1:1 ratio. Fast motions of the outer sphere exceed the magnetic attraction between the two spheres and the inner sphere rotationally displaces relative to the outer sphere. Such rotational displacement is detected by changes in the magnetic field, electric field directed toward a portion of the inner sphere, etc. Rotational displacements sufficient to announce a fall in progress causes the logic controller 22 to send an opening command to the airbag inflator. Standard gyroscopes using spinning tops or other stabilization systems are acceptable for this use but require higher power drain and are more prone to reliability problems.

The gyroscope 16 can be replaced by one or more rotational accelerometers. Each rotational accelerometer can measure rotational acceleration about three axes, X, Y and Z. The rotational accelerometer, such as the one manufactured by ST Microelectronics is capable of providing rotational acceleration information. Taking the integral of the acceleration over time results in the rotational velocity. A single-axis rotational accelerometer is the ST Microelectronics MEMS-based LIS1R02, an analog output accelerometer capable of performing the tasks required for this application. Support circuitry including memory, Analog to Digital conversion, clock, power, and the like are required for such a device. Integrating the rotational velocity data will yield rotational displacement, angle, or distance.

Figure 3B:
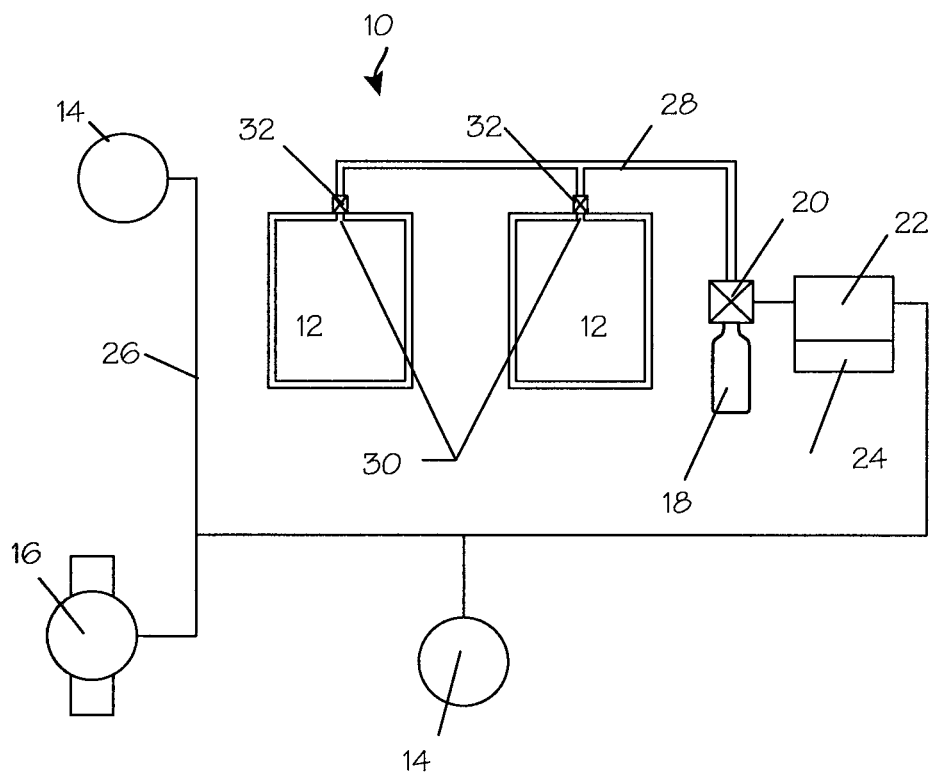
FIG. 3B illustrates another block diagram of the components of a pair of the APG shorts with actuator valves.

FIG. 3B illustrates another block diagram of the components of a pair of the APG shorts with actuator valves. The APG shorts comprise a plurality of cushioning chambers 12, one or more accelerometers 14, one or more gyroscopes 16, a high pressured or compressed gas source 18, an actuable gas valve 20, a logic controller 22, a power supply 24, an electrical bus 26, a gas manifold 28, a plurality of chamber ports 30, and a plurality of one-way valves 32.

The logic controller 22 is a computer and controls all aspects of function of the device from acquiring information from the gyroscopes 16 and the accelerometers 14 to determining whether an actuation condition exists to activating the valve 20 to inflate the chambers 12 to providing notification of the status of the power supply 24 or controller 22 malfunction. The software (not shown) controls the function of the logic controller 22.

The software can be programmed to perform according to predetermined conditions set by the certain parameters. The state of the body as standing, seated or recumbent, can be recognized by a combination of 1) the motions intrinsic to the state; 2) the orientation of torso sensors; and 3) the transitions that lead to the state. The software can be preprogrammed to have a specific program for each state and each potential transition. The individual state and transition programs will recognize normal and abnormal patterns of motion for the state or transition. The program for each state will be triggered either by the end of the transition to that state or the observation of signature motion for the state. The transitional programs will be triggered by the observation of signature torso motions that indicate the possibility of a transition between one state and another. New logic programs can be triggered within the logic controller based upon the state of the patient or on the observation of a transition between states. The sensors can be recalibrated based on the activity or position of the patient's body, and without reference to any external standard. The range of normal trajectories during each of the transitions is preprogrammed into the logic controller. Downward motions of the torso that do not correspond to the preprogrammed parameters for a given transition due to an abnormal sequence, acceleration of trajectory are recognized as falls. The delineation of the predetermined range of normal signature motions for each state can be programmed during a training phase.

The logic controller can be programmed to use threshold accelerations to detect an actual fall and eliminate false positives. The threshold accelerations can also be combined with vertical displacement to create an additional program where the deployment thresholds for accelerations and for estimated vertical displacements are used together. Deployment can be indicated by accelerations above thresholds that vary appropriately with the orientation of the patient's torso. The threshold accelerations can utilize vertical and lateral accelerations either as a total acceleration relative to gravity, total acceleration including gravity, or as separate thresholds on either vertical or lateral accelerations.

The preprogrammed phases are the standing state (S1), the seated state (S2) and the recumbent state (S3). The standing state (S1) is recognized if the sensors are in a vertical alignment, a walking signature motion is observed and there is no transition or fall. The standing state is also recognized to exist if a seated state to standing transition has been observed and no fall has occurred during the transition. Patients reach the seated state (S2) by transition from either S1 or from S3. A person will be considered to be in S2, triggering the program for this state if the torso is within 45 degrees of vertical and if an S1 to S2 transition has been observed without a fall or a further transition to recumbency. A person who is in the seated state and who shows no transition to standing or to recumbency will be considered to be remaining in S2. A person will also be regarded in the seated state if a transition from S3 to S2 has been observed. It is characteristic of the seated state that the pelvis will be vertically stable although the upper torso tilts over a broad range. A person will be recognized as being in the recumbent state if the torso orientation is within about 20 degrees of horizontal, if the transition from S2 to S3 has been observed and there is no fall. Rotation around the axis of the torso without much change in the magnetometer orientation of the axis is common in the recumbent state.

The logic controller often cannot determine if an observed motion is normal based entirely on the motion signature itself. Before it can interpret the normalcy of a motion, the logic controller must know the context (body state) in which the motion is occurring. The programmed rules by which it judges normal and fall motions will specify the state that the torso was in at the onset of the potentially significant motion. In addition to the recognition of three normal states, the transitions are also recognizable from torso motion. The normal transitions are 1) from the standing state to the seated state; 2) from the seated state to the standing state; 3) from the seated state to the recumbent state; and 4) from the recumbent state to the seated state. The recognition of these transition sequences helps to establish the body states for use of the logic controller. Moreover, because falls can occur during transitions, the logic controller recognizes the pattern of normal transitions between the states and how these differ from fall motions. The individual state and transition programs can recognize normal and abnormal patterns of motion for the state or transition. The program for each state will be triggered either by the end of the transition to that state or by the observation of signature motion for the state.

The transitional programs will be triggered by the observation of signature torso motions that indicate the possibility of a transition between one state and another. The logic controller can be recalibrated based on observed user activity of the body. Sensors can be placed on the user's body in order to program normal and transition states that are unique to the user. For example, where the height of the sensors above the ground when the user is standing are known, the sensors would recognize when the user is walking or standing. If the user is observed going from a standing state to a seated state, that is, if the user went through the transition for assuming the seated position, the approximate height of the sensors could also be inferred once the user has completed the transition and is in the seated state. This is also true for the recumbent position. New programs may be triggered within the logic controller based upon the state of the monitored user or on the observation of a transition between states. Observed torso motions will be referenced to the body state or transition as being normal or abnormal. Parameters will be programmed for allowable motions in each direction for each body-state and transition. The normal range of trajectories during each of the transitions will be established. Downward motions of the torso not corresponding to programmed parameters for a given transition because of an abnormal sequence, acceleration or trajectory will be recognized as falls. The delineation of the normal motion signatures for the standing/walking state, the seated state and the recumbent state for the transition between states are programmed during a training phase.

The fall recognition for the S1 state includes several rules. First, forward, right anterior torso tilting of up to 90 degrees that is not accompanied by axial acceleration beyond a programmed limit is permitted, within 30 to 45 degrees on either side of the direct anteroposterior axis. Such tilting may signal either a reach or the beginning of a transition from the standing state to the sitting state. This rule can be modified by acceleration and trajectory parameters during training. Second, posterolateral, or lateral tilting of the torso more than 30 to 45 degrees on either side of the directed anteroposterior line, accompanied by any pelvic/torso descent is defined as a fall. Any posterior or postcerolateral descent of greater that 10 inches is defined as a fall unless the prior transition program for standing state to sitting state has been activated. Third, Cephalad, axial acceleration of the torso beyond programmed limits, or accompanied by a downward motion is defined as a fall. Fourth, Kyphosis, the use of a cane or a walker may set, as normal, a slight unilateral tilt. Observation of these variations during the training phase will allow the user's customary posture to be programmed as well as the normal vertical posture. Fifth, to accommodate elevator travel, direct vertical ascent and descent will be accepted as a normal motion for a person in the standing state. Sixth, the motion of walking will be recognized by characteristic, low amplitude, vertical undulations and forward motion. Because the length of stride in most elderly individuals is fixed, the frequency of the undulations will serve as an indicator of the rate of anterior motion.

The parameters for S2 permit torso motions that are categorically abnormal in S1. The program for S2 will allow for a wide range of torso tilting in the posterior or lateral directions, down to 90 degrees or more, because such motions are associated with the normal transition from the seated state to the recumbent state. Anterior torso tilting in the seated state is also tolerated up to 90 degrees, as long as the pelvis does not descend and the vertical orientation of the torso is not reversed. These parameters can be modified by observation made during the training phase. However, the program for the seated state will allow almost any motion except a reversal of the vertical orientation of the sensors, excessive axial acceleration in the cephalad direction or the shock of a collision. Motions of wheelchair or automobile travel will be accepted as normal by the S@ program. Also, direct vertical ascent or descent, as in an elevator, will also be accepted as normal by the S2 program.

The program for the S3 state will recognize the height of the sensors as being 24 inches above the ground and any descent of greater than 6 inches within 5 seconds of a torso rotation will be recognized as a fall. As for all of the state and transitional programs, normal parameters will be established during a training phase.

The transitional programs can recognize stereotypical human motions that characterize the passages between S1, S2 and S3. The recognition by the logic circuit of motion signatures that indicate a possible transition will trigger the activity of the program covering possible transitions. The transition programs vary according to the steady state from which the transition originates. Torso motions observed during the possible transitions will be compared to normal and expected sequences and trajectory parameters that have been programmed into the logic circuit during the training phase. Motions that depart by reasons of sequence, acceleration, velocity, distance, rotation or trajectory from the normal parameters may be recognized as falls. Falls can be recognized by abnormal motions during transitions or during steady states. The accurate recognition of the onset of a possible transition necessary to initiate the program for allowable motions during the passage from one state to another and to distinguish the new state the torso is entering.

Two important principles are involved in distinguishing the S1 to S2 transition from a fall. The first is that people generally walk forward and sit down backward. The second is that controlled transitions between S1 and S2 require a sustained anterior tilting of the torso to maintain the center of gravity over the thighs during a sitting descent. Thus, an anterior tilt of the torso of between 15 and 45 degrees in a standing position is the necessary, although not sufficient, condition of a normal, potential transition from S1 to S2. It is this motion that permits the slow, controlled, posterior descent of the torso over a relatively steep trajectory. It is virtually impossible to pass normally from S1 to S2 without this tilted posture. The degree of the anterior torso tilt and the trajectory of the posterior descent are both likely consistent from one S1-S2 transition to another for an individual, and they may not vary much between individuals of similar age, size and conditioning. The controlled posterior descent of the pelvis in the S1-S2 transition is slower than the descent of most posterior falls. The logic controller is programmed to recognize a possible transition from S1 to S2 by an anterior tilting motion of the torso greater than 15 to 45 degrees, or within a range that has been determined during the training mode to be normal for the user. The tilting of the torso beyond a prescribed threshold triggers the transition program for S1-S2. Falls are distinguished by departures in acceleration or trajectory from the norms that are programmed. Posterior descent without the expected degree of anterior torso lift are recognized as falls. The torso tilt required by the transition from standing to seated state may be anterior or slightly anterolateral (within 45 degrees of a direct A-P axis). The transition program will not recognize lateral or posterolateral tilting of the torso as S1-S2 transitional movements. Unique sitting techniques to pass through the transition from S1 to S2 can be programmed during the training phase as a normal transition to sitting for the individual. Additionally, the normal sitting motion for users who walk with a cane or a walker can also be recognized during the training phase. However, in every case, a marked anterior tilting of the torso is an essential condition for a controlled posterior torso descent and is the signature motion to trigger the S1-S2 transition program. The transition from S1-S2 will be regarded as complete when the following conditions are met: 1) the pelvis has reached an end of its descent and there is a signature recoil observed; and 2) the anterior tilt of the torso is reversed. Once the transition is completed and the patient is recognized as being in the S2 state, the S2 program will run until interrupted by another potential transition or fall.

The seated state allows for two possible transitions. A seated person will either fulfill the stereotypical transition for assumption of S3 or will attempt to transition to S1. The anterior tilting motion of the torso is necessary in the ascending transition from S2 to S1. Therefore, the transition from S2 to S1 requires a signature anterior tilt of the torso of more than 30 degrees. This motion by a user in S2 signals a possible transition to S1. The transition program is initiated when there is an upward and forward acceleration of the forward-tilted torso. Pelvic rotation of 15 to 30 degrees may accompany the attempt to stand. Falls during the S2-S1 transition are recognized by abrupt forward pitching with cephalad acceleration along the axis of the torso or lateral accelerations outside the expected parameters for the normal motion of rising from the seated state. The end of the transition from S2 to S1 is recognized when one of the three conditions is met: 1) the ascent stops after a normal trajectory without any intervening fall; 2) when the torso tilt is reversed and the normal vertical state of the torso is restored; or 3) when the walking motion is observed.

The transition from S2 to S3 is activated when the torso has tilted more than about 60 degrees laterally or posteriorly from the vertical of the seated state. The torso may move through an eventual arc of 90 degrees from vertical, either to the side or to the back. The completion of transition from S2-S3 is recognized when the upper portion of the torso has ceased descending and the orientation of the axis of the torso is horizontal. As the transition to a sitting state is completed or nears completion, and possibly before the descent of the torso has stopped, a reclining person may tilt sideways or backward to transition to the recumbent state. The transition program recognizes this as normal and therefore a rule may be programmed that lateral tilting of the torso is permitted in the last stages of an otherwise normal S1-S2 transition.

The transition from the recumbent state to the sitting state must take into account the weakness of the anterior abdominal muscles. In order to reach the state from recumbency, the patient must turn on one side or another and lift the torso slightly using the arms for support. Next, one or both legs are dropped over the side of the bed and the torso arcs upward to an erect position. The end of the transition from the recumbent to sitting state will be recognized when the upward motion ceases and the torso has reached an almost vertical orientation. At this point it will be common to see the beginning of the S2-S1 transition.

The crucial transitions from S2 to S1 and S1 to S2 which involve a change in the height of the entire torso, are characterized by an initial forward tilting of the torso beyond a threshold which triggers the transitional program. Despite this anterior tilt, anterior and downward acceleration of the torso is not characteristic of any of the transitional movements.

Although an anterior tilt of the torso is crucial to the initialization of the possible transition programs between S1 and S2, there are several instances in which such anterior tilting could be caused by actions other than the intended transition from one state to another. The program can anticipate the stereotypical follow-on motions to complete the transition to a different state. However, pseudotransitions may occur. Pseudotransitions are distinguished from real standing to sit or sit to stand transitions by the absence of significant pelvic descent from S1 or upward pelvic movement from S2 along expected trajectories and within a few seconds.

Pseudotransitions are distinguished from falls by the absence of acceleration along abnormal descending trajectories. Without descent or rise of the torso there can be no transition from one state to the other. Thus, an S1 to S2 transition cannot be occurring if the torso does not descend along the trajectory expected for the distance and the time required in the sitting transition. Similarly, an S2 to S1 transition cannot exist if the torso does not rise a distance necessary to reach the standing state. Therefore, pseudotransitions are distinguished from real transitions by this means.

The transition programs have a time limit based on the expectation of either completion of the change in state or of a fall within a few seconds of the onset of the anterior torso tilt. Torso tilt unaccompanied by change in the vertical height of the torso are recognized as a pseudotransition if the transition algorithm is not completed within a few seconds after the torso tilt is observed. In the case of a pseudotransition, the program will revert to the status reset, that is the state in which the user was known to be prior to the torso tilt. The degree of torso tilt in the anterior direction that define a possible transition are determined by observation during the training mode.

A separate type of pseudotransition may occur in the S2 to S1 transition program. If a user in the S2 state attempts to stand, that is, tilts the torso forward and drive the pelvis forward and upward, weakness or ataxia may cause the patient to pitch forward or laterally. These motions are recognized by the program as falls during the transition.

In addition to the steady state programs for S1, S2 and S3 and the transitional programs which recognize the movement between one state and another, several harbinger motions may also be recognized. These harbinger motions have a high probability of leading to a fall and which, even absent of falling motion, may deploy protective measures. These harbinger motions consist of: 1) backward walking of more than one or two steps with or without torso rotation; 2) wobbling or unsteady anterior-posterior or side-to-side instability of the user in the S1 state; 3) sudden impact acceleration or deceleration reflecting a collision with an object or another person; and 4) abnormally rapid walking with a forward torso tilt. An acceptable rate of walking based on the number of low amplitude undulations per minute will be programmed into the S1 program during the training phase so that rapid walking patterns can be recognized.

The logic controller is programmed to recognize potential fall related motions in each steady state and transition program. Falls are recognized as accelerations, trajectories or rotations outside the accepted parameters for normal activities. Almost all falls are characterized by motions that depart from normal trajectory parameters in direction, acceleration, velocity, duration or rotation and by the absence of preliminary, normal, transition motions. Falls are characterized as uncontrolled descents of the center of mass and will therefore lack the stereotypical postures consistent with controlled descent. It is this absence of controlling posture with results in the abnormal velocities and directions of descent. Because fall motions cannot themselves be trained into the state and transition programs, they will be defined as significant departures from the normal trajectories.

When falls arise out of the S1 state or occur during transition from S1 to S2 or S2 to S1, most human falls are characterized by one of three easily recognizable, categorically abnormal motions. The first of these abnormal motions is lateral and downward torso acceleration beyond the parameters of normal motion for a person in the S1 state or in an S1 to S2 or S2 to S1 transition. Such fall motions may be directly lateral, anterolateral or posterolateral. They occur along trajectories that are not observed in the normal S1 or transitional states. The second categorically abnormal motion for a person in the S1 state or in a transition is an anterior pitch in which the torso accelerates cephalad along its axis at a rate not seen in normal states or transitions. This sort of forward pitching fall may occur during walking or during an attempt to rise from a seated state. The third motion that is categorically abnormal from the S1 state is a backward and downward motion of the torso without the prior transitional movement of a forward torso tilt of at least 15 to 30 degrees. Such posterior falls occur along abnormal trajectories and often at high speed. The upper torso is either less tilted anteriorly than is necessary for a controlled descent or is actually tilted posteriorly, accelerating the fall motion. These fall types from the S1 state may result from tripping and pitching forward or from staggering and collapsing backward and sideways. The classic "heel slip" fall results in a backward or posterolateral and downward motion of the torso at very high speed.

The transition from S2 to S1 is one of the most common occasions of injurious falls in the elderly, commonly occurring at night. As a person attempts to rise from a recumbency to sitting then to standing, he may fall over anteriorly or laterally. If the predicted S2-S1 sequence is interrupted by an abrupt, lateral or downward or anterior and downward acceleration, a fall is recognized. If, on the other hand, the transition-interrupting acceleration is posterior and downward, to a level not lower than the original seated state, a pseudotransition will be recognized. Thus, interruption of the S1-S2 transition either by a fall or a pseudotransition can be recognized. This distinction depends on the direction, distance and velocity of the descent. If the user reaches S1, as evidenced by a vertical position of the sensors after the arrest of normal upward movement or the recognition of the walking gait, the S1 program will be activated and any subsequent descent along an abnormal trajectory will be recognized instantly as a fall.

Falls from the S2 state may take the form of a forward pitch, or a lateral or posterior fall from a chair or other platform. Such falls can be detected by the S2 program if there is a reversal of the vertical orientation of the torso or excessive axial acceleration of the tilted torso. Falls from the seated state, as opposed to falls arising during transitions, are uncommon and usually not dangerous.

Falls from the S3 will involve rotations around the axis of the torso followed by descent of part, or all, of the torso. These falls from bed or from a couch are generally low energy and can be detected by passage through a threshold distance from the floor. Many un-witnessed falls that result in the patient being found on the floor next to his bed actually occur during attempted transitions to S1, not tumbling out of bed.

A person is recognized in a seated state if the torso is within 45 degrees of vertical and if a standing state to seated state transition has been observed without a fall or a further transition to recumbency. In a seated state, the pelvis will be vertically stable although the upper torso tilts over a broad range. A person is recognized in a standing state where there is vertical alignment of the sensors after a transition from a seated or recumbent state, a walking signature motion is observed and there is no transition or fall. A person is recognized in a recumbent state if the torso orientation is within about 20 degrees of horizontal, if the transition from sitting to recumbency has been observed and there is no fall. Rotation around the axis of the torso without much change in the orientation of the axis is also common in the recumbent state. Falls are recognized as downward motions of the torso that do not correspond to the preprogrammed parameters for a given transition due to an abnormal sequence, acceleration or trajectory.

The logic controller can also be programmed for fall detection of accidental falls of a rider of a horse, bicycle, motorcycle, or the like. The sensors may be used to track the attitude, orientation, accelerations and three-dimensional trajectories of the rider and the cycle or horse. The logic controller can be programmed to compare these attitudes, orientations and trajectories for the purpose of determining whether they are normal or abnormal. Movement tending to produce a wide separation of the lower torso of the rider from the vehicle is considered abnormal and indicative of descent from the horse, bicycle or motorcycle.

The logic controller can be programmed to determine whether an equestrian, bicyclist or motorcyclist is falling or is otherwise in danger because of extreme lateral, forward or backward attitude and acceleration when the rider and vehicle are falling together. This determination can be made even when the animal or vehicle and rider are going through complex patterns of radical acceleration and deceleration in multiple dimensions in order to deploy devices capable of protecting the rider from injuries caused by impact with the ground or objects above the ground.

The logic controller is programmed to reliably distinguish between the normal patterns of motion in cycling or horseback riding and those of accidents associated with these activities. The lower torso of the rider of a moving bicycle, motorcycle or animal normally travels through space as a functional conjugate of the vehicle or animal. Relatively slight variations are caused by bouncing or by standing upon the pedals or in the stirrups. The motion of the rider's lower torso closely mirrors the anterior-posterior orientation, acceleration, velocity and three-dimensional trajectory of the central frame of the vehicle or torso of the animal while the vehicle or animal is in motion. This is true even if the animal and rider are jumping together over hurdles or the motorcycle rider is driving at high speed around curves or over bumpy terrain. The upper torso of the rider may tilt forward, laterally or even backward, either to reduce aerodynamic drag or to balance the forces placed on it by the motions of the vehicle. Despite this, the lower end of the torso maintains a predictable, close relationship with the vehicle or animal. The gluteal area of the rider need not be in actual contact with the seat or saddle for this relationship to exist. The parameters governing this relationship can be programmed into a logic controller. Certain types of deviations detected while a cycle or animal is in motion can be recognized as falls.

The motions of the cycle or horse and of the lower torso of the rider can be independently tracked using inertial, orientation sensors. A comparison of these motions can be made by the programmed logic controller. Two or more sensors or multiple, individual, uni-axial accelerometers, gyroscopes and magnetometers may be used. The sensors may be separated from each other in such a way as to be mounted or embedded in a belt, collar or other wearable article that follows body contours in three dimensions. The individual sensor elements can be linked electrically so that they constitute a multifunction, three-dimensional, orientation sensor.

At least one orientation sensor is placed on the torso of the rider at or near the midline, preferably at the level of the lower lumbar spine. This sensor will reflect the attitude, orientation, acceleration, velocity, rotation and three-dimensional trajectory of the torso of the rider. The sensor is capable of transmitting its data to a logic controller. Other sensors may be placed elsewhere on the torso. A second sensor can be placed in or on the frame or seat of the bicycle or motorcycle or on the torso or saddle of a horse. This sensor is used to track the attitude, orientation, acceleration, velocity, and three-dimensional trajectory of the center of the bicycle, motorcycle or horse. This sensor is capable of transmitting data to a logic controller. The torso of the rider and the frame of the motorcycle or bicycle or the torso of the horse will each be represented as a simple geometric solid. Orientation sensors placed on the torso of the rider and the frame of the bicycle or torso of the animal independently characterize the orientation, attitude, trajectory and acceleration of each. Much of the motion pattern involved with mounting a cycle or a horse is stereotypical, for example, it is a common human behavior that, after straddling the cycle or horse, the rider will center the buttocks on the seat so that pressure is comfortably distributed on the gluteal area. This stereotypical centering maneuver can be used to establish the midline relationship of the sensor on the body of the rider with that on the vehicle or animal.

Information from the sensors is transmitted to the logic controller, which is programmed to compare the observed attitude and three-dimensional trajectories of the rider with that of the vehicle or animal. A rule-based logic program defines the allowable degree of variation between the acceleration, orientation and trajectory of the rider and those of the vehicle or animal. The logic controller is programmed to recognize and compare the independent, three-dimensional motions of the rider and those of the vehicle or animal. Divergence of the velocities, orientations, accelerations, rotations or three-dimensional trajectories of the rider and the vehicle beyond programmed limits will be recognized by the logic controller as evolving falls.

Beyond the detection of incipient ejection of the rider from the vehicle by recognizing dis-conjugation between the motions of the rider and those of the cycle or horse, the logic controller is programmed to recognize orientations, attitudes, rotational accelerations, trajectories, oscillations or other motions of the vehicle that are inconsistent with normal, controlled driving. The pitch, roll and yaw of the cycle or animal, together with the rate of change in these variables will be continuously monitored by the logic circuit. Abnormal attitude, orientation or trajectory, combined with acceleration of the abnormality of the attitude of the cycle or animal beyond programmed limits will also be recognized as evolving accidents. This recognition can be made even if the sensors on the rider indicate no significant disconjugation between the motions of the cycle or animal and those of the rider. When a detection of abnormal motion or attitude is made, the logic controller will send out a signal to deploy protective measures. Some examples of detection of abnormal motion or attitude are as follows: A horse rears and falls backward, sideways and downward. The rider's torso moves downward with unacceptable acceleration; a Motorcycle traveling at high speed shows abrupt side to side oscillation and abrupt changes in heading, indicating an attempt of the rider to gain control; Yaw angle of the motorcycle passes 45° and shows no slowing or/and acceleration in the rate of yaw; extreme yaw the motorcycle is succeeded by a lateral impact The system may include sensors that determine the distance between the motorcycle, and fixed objects in the environment or an imaging program to determine where the edges of the fixed object are. Data from the sensors can indicate the distance from objects and the rate of closure. This information can be used in conjunction with data regarding the velocity of the motorcycle, its orientation and its heading. The logic controller can be programmed to recognize combinations of motorcycle speed, heading, attitude, proximity to an object and rate of closure upon that object that would exceed the possibilities of avoiding an impact by evasive maneuvers or braking to deploy the protective measures.

Riders do not just fall off motorcycles or horses. They are ejected as a result of radical changes in the acceleration, attitude or trajectory of the cycle or horse. Falls and ejections thus occur in the context of violent motions of the cycle or animal, most typically, an abrupt deceleration. The circumstances surrounding a fall or ejection are very different therefore from the relative absence of motion of the cycle or animal during normal dismounting. It is a rule that will be programmed into the logic circuit that the disconjugate motions, characteristic of dismounting are permissible only when the vehicle or animal has been gradually decelerated to a velocity less than 2 miles an hour.

The motions of a rider associated with dismounting from a bicycle, motorcycle or horse represent stereotypical patterns. They are accomplished with far lower acceleration than falls and are carried out with predictable patterns of torso attitude, direction, rotation, and trajectory. Algorithmic logic for dismounting is integrated into the program run by the logic controller. For example, normal dismounting from a horse would encompass the following rules: 1.) The animal is at rest, that is, is traveling less than 2 miles/hour in any direction; 2.) No pitching, rolling or yawing of the torso of the animal behind 5° is occurring; 3.) torso of the rider is generally upright and tilted forward; 4.) a slow rotation of the torso of the rider, covering 90 to 120° is observed; 5.) a downward acceleration of the, vertical torso of the rider with an acceleration of less than 1 g for less than 4 feet is observed. The logic controller is programmed to distinguish these normal behaviors from the motions of the rider and the cycle or animal associated with falls or ejections.

A person mounting a motorcycle, bicycle or horse also exhibits highly stereotypical behaviors. Patterns of torso motion associated with mounting a motorcycle or horse are the most important. Those for beginning a ride on a bicycle are slightly different. While the writer of a motorcycle or force will mount, while the machine or animal is essentially at rest, a bicyclist may stand on the pedal and push the bike forward to some slight forward velocity before swinging a leg over and sitting.

As another example of normal disconjugate movement, racing bicyclists often stand up on the pedals and oscillate the bicycle back and forth underneath them during the violent exertion of sprinting. However, even during this radical effort, predictable patterns of velocity, orientation, attitude and three-dimensional trajectory will exist between the lower torso of the rider and the frame of the bicycle. They are generally traveling within a framework of similar orientation, in the same direction and at the same forward speed. The logic controller can be programmed to recognize even these complicated normal motion patterns and yet recognize the degrees of disconjugation or excessive tilting of both the bicycle and rider that indicate a fall.

In contrast, when a rider falls off, or is ejected from, the cycle or animal, a rapid, radical disconjugation of the three-dimensional trajectories of the rider's torso and that of the vehicle or animal will occur. The disconjugation of the orientation, attitude and trajectories will be of a greater degree and will last longer than normal disconjugate movement. This disconjugate movement would occur in the context of violent changes in acceleration of the cycle or animal. For example, radical rolling pitching or yawing of the animal is observed. Abrupt deceleration is observed. The rider accelerating with anteriorly pitched and yawing attitude from the animal. A rule-based logic controller can be programmed to recognize the patterns immediately.

Some additional examples include the following:

The cycle or horse might abruptly decelerate while the rider continues accelerating forward or laterally. Within a few milliseconds, the disconjugate movement would be recognizable as abnormal.

In the case of an impact of a car against the side of a bicycle or motorcycle, an abrupt, high-energy, lateral acceleration spike might be detected by sensors on both the rider and the cycle, followed by disconjugate movements or an abnormally rapid yawing motion of the both the cycle and rider.

A rider being thrown from a rearing horse would show unusual upward and backward pitching acceleration, initially in concert with the motion of the torso of the animal. This concerted motion would then be followed by a disconjugate motion if the rider falls toward the ground. Even the motions of the lower torso of a cowboy on a bucking bronco or bull would closely follow those of the animal until he is thrown. These motion patterns would be easily recognized by a programmed logic circuit receiving input from orientation sensors on the rider and animal.

Certain types of motorcycle accidents, especially sliding out, in which the motorcyclist deliberately or unavoidably brings the side of the vehicle into contact with the ground to avoid a collision, will not initially be characterized by disconjugate motion between the rider and the bike. Nonetheless, characteristic motion signatures having to do with extreme lateral tilt, lateral impact, unexpected trajectories and rotations of both the rider and the cycle would allow this type of accident to be recognized early in its evolution by a logic circuit.

Typically, accidental falls represent 1 standard deviation departures from normal descent of the center of mass of torso, attitude, trajectory, acceleration/rate, velocity, duration of free fall, acceleration/rate of torso roll and acceleration/rate of torso yaw. Failure to rise after a fall can be another programmed element for completed fall detection. When the look-back function of the programmed logic controller has recognized a descent of the center of mass along an abnormal trajectory, at an excessively rapid vertical acceleration/rate, roll acceleration/rate and yaw acceleration/rate, followed by an impact greater than 1 standard deviation above the impact force observed in the training phase during a normal stand-to-it transition, a presumptive fall is assumed to have occurred. If the torso attitude following this fall is greater than 45 degrees off vertical, a completed fall will be confirmed by the logic controller. Thereafter, failure of the monitored subject to show upward acceleration of a forward-pitched torso within a prescribed period of time will be interpreted as a completed fall with failure to rise.

The actuable gas valve 20 is motor operated, or opened by melting, moving, or dissolution of a plug. The melting, moving, or dissolution of the plug can be accomplished using electrical energy delivered from the power supply 24 and controlled by the logic controller 22 and delivered to the actuable gas valve 20 by the electrical bus 26. The valve 20 can be a ball valve, erodeable membrane, needle valve, gate valve, or any other suitable valve that can be fully or partially opened at high speed when activation occurs.

Figure 4:
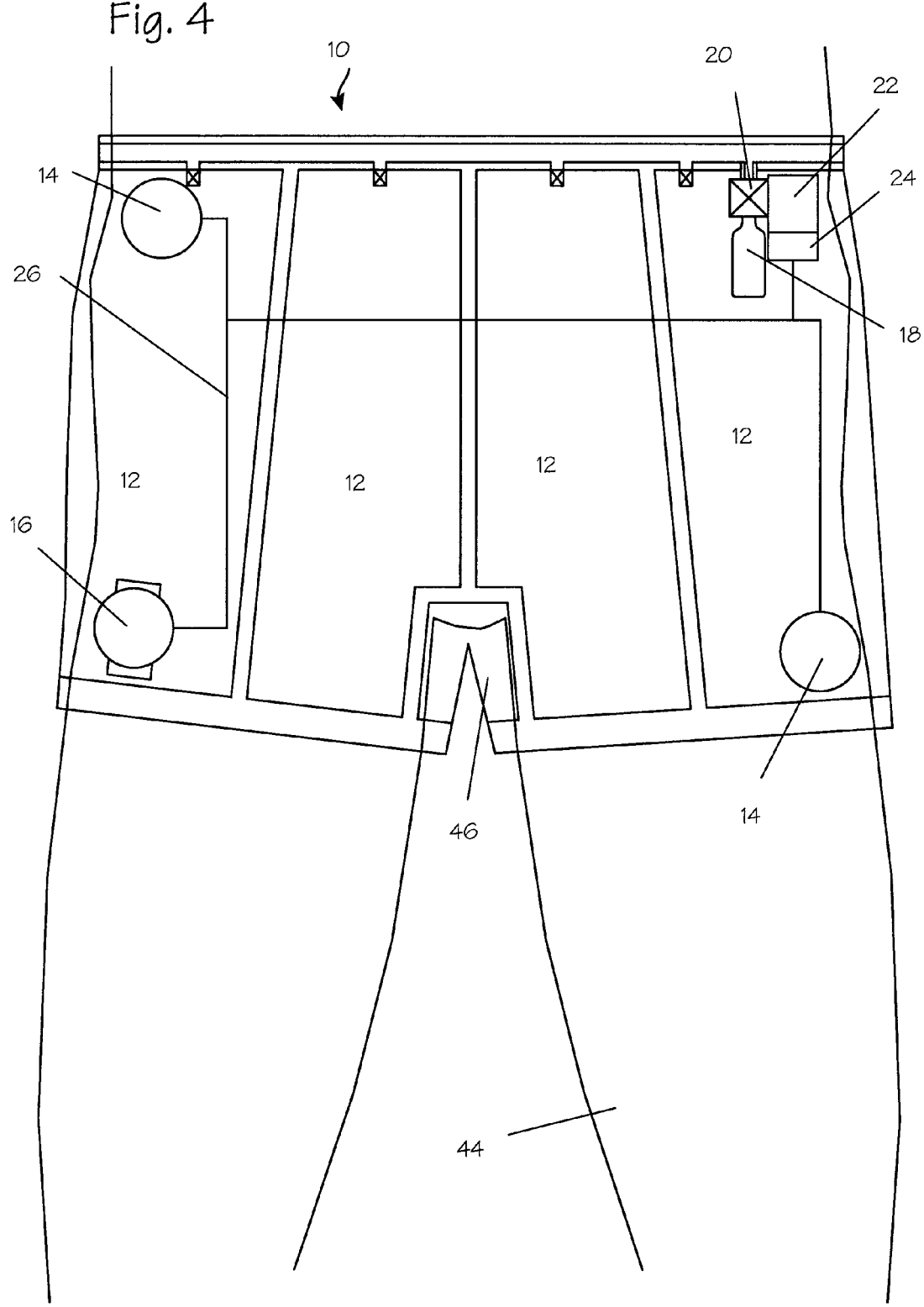
FIG. 4 illustrates a front view of a pair of APG shorts being worn by an individual.

FIG. 4 illustrates a front view of a person 44 wearing the APG shorts 10. The APG shorts 10 are deflated in this illustration. The APG shorts 10 further comprise a plurality of separate inflatable chambers 12, one or more accelerometers 14, one or more gyroscopes 16, a high pressure or compressed gas source 18, an actuable gas valve 20, a logic controller 22, a power supply 24, an electrical bus 26 and one or more non-inflatable regions 46. The APG shorts 10 cover the pelvis, hips and upper femur of the person 44. The non-inflatable region 46 shown in FIG. 4 is in the area of the crotch where high-speed inflation could cause damage to genital organs. A falling person would not normally need protection at the front of the garment in the crotch area because this is an area, which would not receive any impact from the most probable types of fall.

FIG. 5A illustrates a side view of a person wearing the APG shorts 10. The person 44 is standing in this illustration. Outer clothing is not shown but could be worn over the APG shorts 10.

FIG. 5B illustrates a side view of a person 44 wearing a pair of APG shorts 10. The person 44 in this illustration has slipped from a standing position and is in the process of falling. The APG shorts 10 have detected that an unusually high rotation rate is occurring and that gravitational acceleration has suddenly diminished more than in half. As a result of this information, the APG shorts 10 are in the process of inflating.

FIG. 5C illustrates a side view of a person 44 wearing a pair of APG shorts 10. The person has completely fallen and has landed on the ground with the greatest impact being absorbed by the buttocks and hip area. The APG shorts 10 are fully inflated to their operational pressure. The inflated APG shorts 10 prevent direct impact between the person's 44 hip or pelvis and the ground. A fractured pelvis is avoided in this circumstance. The entire fall takes place in approximately 0.25 seconds.

Figure 6:
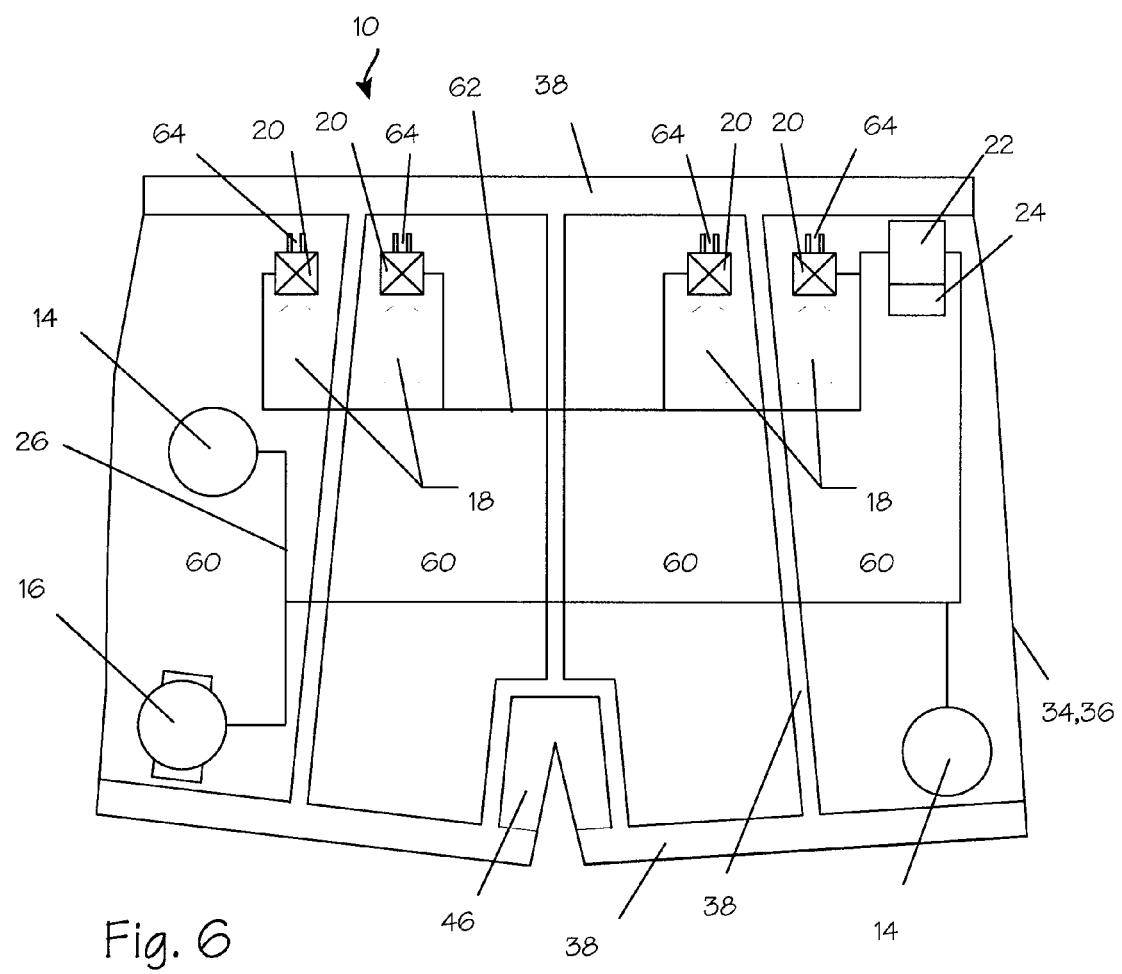
FIG. 6 illustrates a pair of APG shorts with distributed activation mechanisms.

FIG. 6 illustrates a pair of APG shorts 10 comprising a plurality of totally isolated or separated inflatable compartments 60, a plurality of sources of high pressure or compressed gas 18, a plurality of actuable gas valves 20, a plurality of gas vents 64, a system electrical bus 26, a system electrical output bus 62, a logic controller 22, a power supply 24, an inner fabric layer 34, an outer fabric layer 36, one or more accelerometers 14, one or more optional gyroscopes 16. The separate inflatable compartments 60 may be comprised of the inner gas impermeable fabric layer 34, the outer gas impermeable fabric layer 36 and a plurality of gas impermeable seals 38.

Referring to FIG. 6 and FIG. 1, the inflatable compartments 60, in FIG. 6, differ from the inflatable compartments 12 of FIG. 1 in that they are totally isolated and do not have the manifolds 28 or other passageways leading from the compressed gas source 60 to the compartment 60. The reaction time of the device shown in FIG. 6 is much quicker than that of the device of FIG. 1 in that the gas does not have to travel through tubes or passageways to reach a remote chamber 12. Instead, the gas is vented directly into the chamber 60. A plurality of airbag inflators are required, one for each gas source 18. The triggering energy for the airbag inflators is routed through the electrical output bus 62. The logic controller 22, the power supply 24, the accelerometers 14, the gyroscopes 16 and the rest of the system bus 26 are as described as in FIG. 1.

Alternatively, the device as illustrated in FIG. 6 may have a high pressure or compressed gas source 18 that is a solid or liquid material that is catalytically or pyrotechnically made to undergo a reaction, such as oxidation, that releases the correct amount of gas into the compartment 60 required to develop the specified pressure. Such pyrotechnic or catalytic devices have the property of being much smaller and lighter than a compressed gas canister and would not be visible, protrusive, or obtrusive.

The plurality of isolated chambers 60 are especially advantageous for a large APG garment such as a coat or trousers. It is not as necessary for a small garment such as a collar or a pair of shorts. It is still advantageous, for reasons of bulk and accelerated activation times, to use distributed inflation systems as described in FIG. 6 in small garments.

Figure 7:
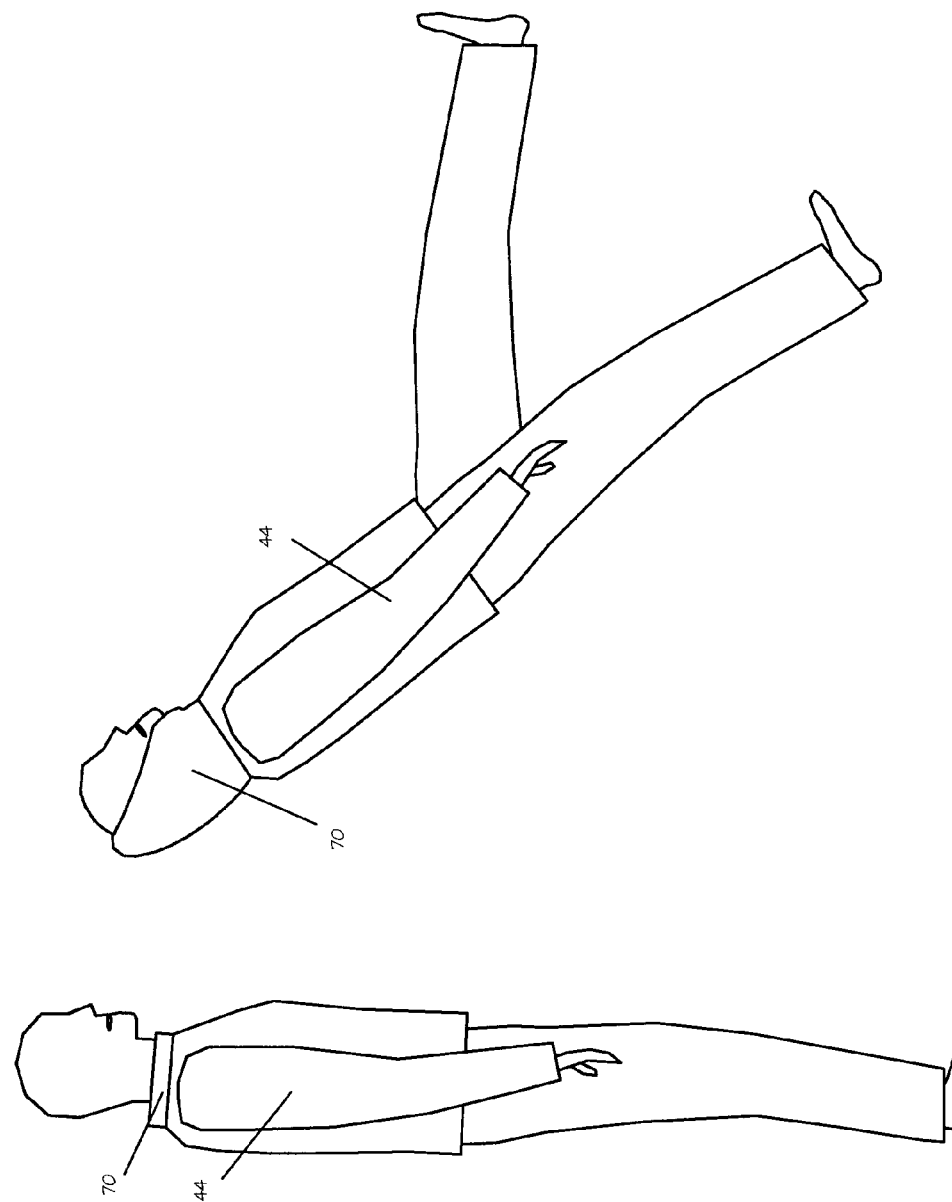
FIG. 7A illustrates an APG collar on a jacket prior to activation.
FIG. 7B illustrates an APG collar on a jacket following activation.

FIG. 7A illustrates an active protective garment in the configuration of an APG collar 70. The APG collar 70 is permanently affixed or integral to a standard jacket, coat, or vest, or the APG collar can be removably affixed to the jacket, coat, or vest. The APG collar 70, shown in FIG. 7A, is in its deflated, unactivated state. Referring to FIGS. 1A and 7A, the APG collar 70 comprises all the components of the APG shorts 10 but is specifically configured to protect the neck and at least part of the head of the person 44 wearing the APG collar 70. While the APG collar 70 may only need one inflatable chamber or compartment 12, it may have a plurality of such chambers 12 to improve pressure distribution throughout the APG collar 70 once activated.

FIG. 7B illustrates the APG collar 70 following activation. The APG collar 70 has activated because the person 44 wearing the APG collar 70 has begun to fall. Rotational and acceleration sensors in the APG collar 70 have determined that a fall is in progress and the logic controller has sent a signal to open the valve to the compressed gas canister so that the compartments 12 fill to the pre-determined pressure. The APG collar 70 has expanded upward to protect the back of the head, the side of the head, and the neck from impact. In addition, the APG collar 70 provides stiffness to the neck and head to minimize the risk of cervical spinal injuries by preventing torsional stress to the upper spine. The APG collar 70 expands upward under the chin and, in conjunction with the rear and side head supports, keep the neck straight and aligned during an impact.

The face may be protected by a compartment 12 of the APG collar 70 that expands upward at the front of the head. Alternatively, in the APG collar 70, a compartment may be formed inward over the top of the head to provide protection to the top of the head.

A compartment of the APG collar 70 may extend downward along the spine to provide protection and stiffening to the spine during an impact, thus reducing the chance of or extent of spinal injury.

Such an APG collar 70 is a useful adjunct for persons riding bicycles or motorcycles or a person engaging in sports such as skiing, skateboarding, water skiing, snowboarding, and the like. Often participants in these activities prefer not to wear head protection because of style or comfort reasons and the APG collar 70 will still provide these people with impact protection. For these sporting applications, internal pressures and times to activation may need to differ from those when simply falling. Reaction times may need to be on the order of an air bag in a car. Sophisticated algorithms will be required in the logic controller to distinguish between a crash event and normal occurrences during some of these activities.

Figure 8:
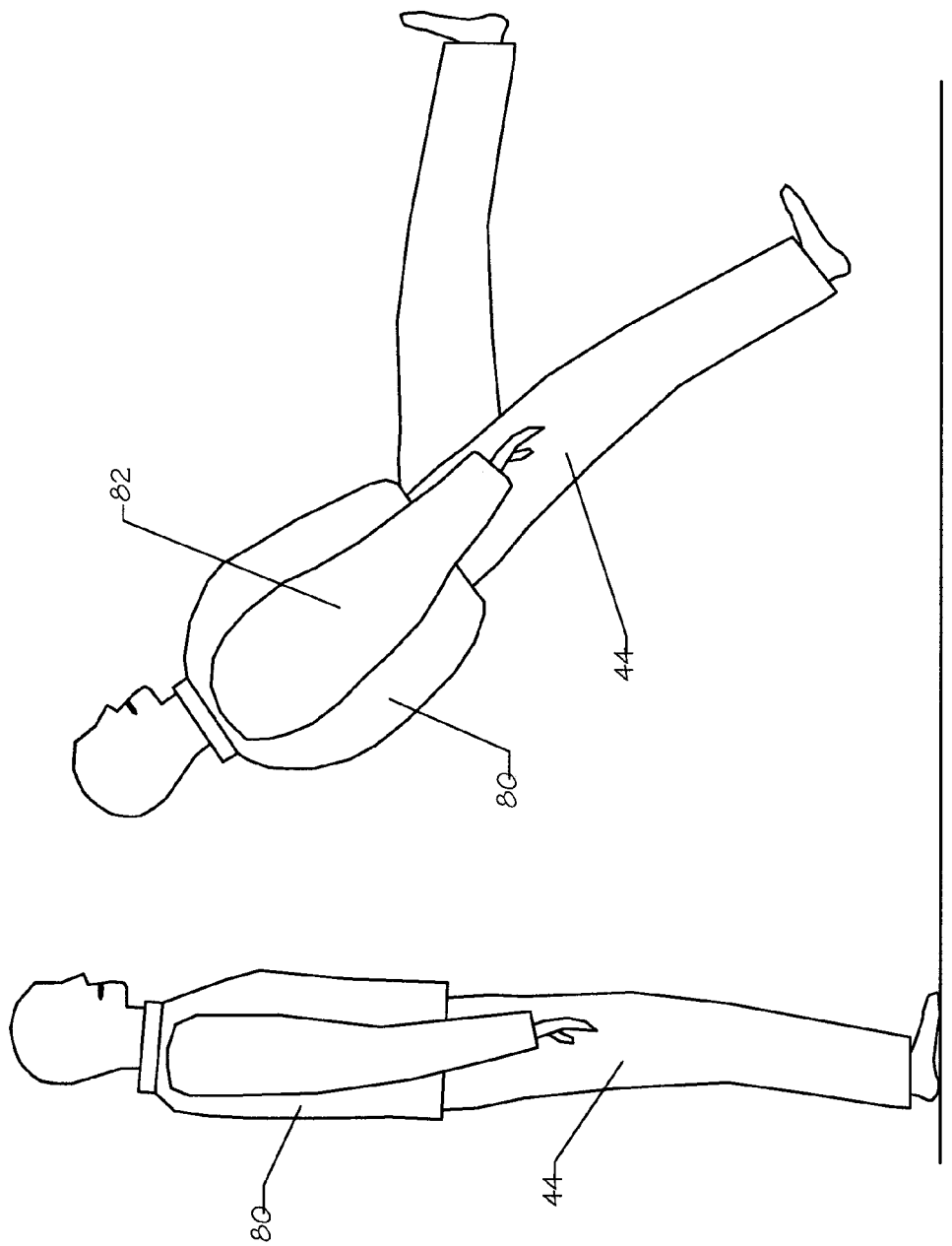
FIG. 8A illustrates an APG jacket prior to activation, according to aspects of an embodiment of the invention.
FIG. 8B illustrates an APG jacket after activation.

FIG. 8A illustrates a deflated APG jacket 80 being worn by an individual 44. The APG jacket 80 is normal in appearance and can be styled to match any trend or garment design. This APG jacket 80 does not further comprise an APG collar 70 as described in FIGS. 7A and 7B but such an APG collar 70 may be comprised by the APG jacket 80. Referring to FIGS. 1A and 8A, the APG jacket comprises all components specified for the APG shorts 10 of FIG. 1A. Referring to FIGS. 7B and 8B, the operational parameters for the APG jacket 80 are more similar to those for the APG collar 70 than the APG shorts 10 because of high speeds and occasional low gravity events that might be encountered during the activities specified for the APG collar 70.

FIG. 8B illustrates the APG jacket 80 following activation on a person 44 who is falling. The APG jacket 80 has a plurality of compartments 12 that have inflated and will continue to inflate to the specified pressure prior to the person 44 hitting the ground. The APG jacket 80 further comprises arm compartments 82 that have also inflated to protect the wearer 44 from arm impact and potential broken bones.

The APG jacket 80 may be configured as a shirt or undershirt that is completely hidden under outer layers of clothing.

Figure 9:
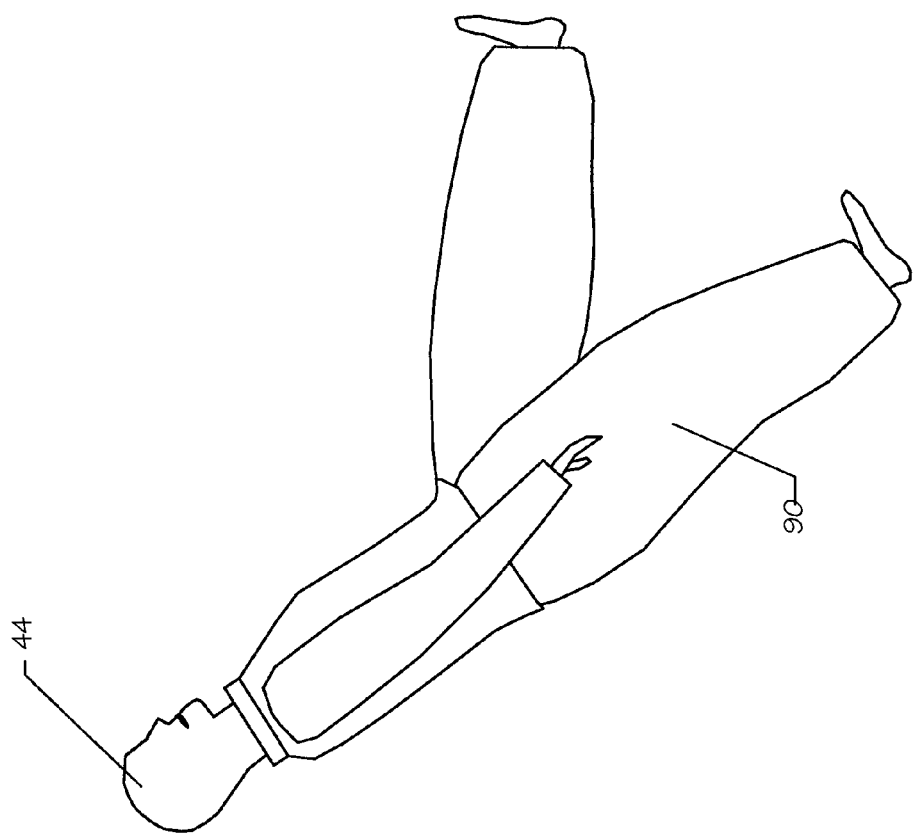
FIG. 9A illustrates a pair of APG trousers prior to activation.
FIG. 9B illustrates a pair of APG trousers following activation.

FIG. 9A illustrates a pair of APG pants 90 being worn by a standing individual 44. Referring to FIGS. 9A and 1A, the APG pants 90 comprise all the elements or components of the APG shorts 10. A greater number of chambers 12 are required for the APG pants 90.

FIG. 9B illustrates the pair of APG pants 90 following activation on a person 44 who is falling. The APG pants 90 have a plurality of compartments 12 that have inflated and will continue to inflate to the specified pressure prior to the person 44 hitting the ground. The APG pants 90 may further comprise a compartment 12 that expands upward from the waist to protect the back and abdomen of the person 44. Such back and abdominal protection protects from impacts and also from torsional stresses that could cause strained back or abdominal muscles or ligaments. The control componentry of the APG pants 90 is affixed to the belt area of the APG pants 90 to maximize mobility, although one or more motion sensors may be placed further down the leg.

The APG pants 90 may be configured as underpants or an undergarment that is worn completely hidden beneath outer layers of clothing.

The material of the garment may be fabricated from fibers that are highly flexible in their unactivated state. Following activation, these fibers become more rigid and provide additional impact, penetration, and skid protection. Such materials are especially useful for motorcycle and bicycle riders that become abraded from falling. Nitinol fibers may be incorporated into the weave of the fabric of the APG garment. When activated, the nitinol is electrically or resistively heated to cause a phase transformation from a martensitic to an austenitic state. The nitinol fibers shorten to tighten up the weave or they pull the weave at a bias to cause the weave to become stiffer. Ohmic or electrical resistive heating of nitinol requires very little time and the response time is less than $\frac{1}{100}$ second.

The nitinol may also be used to cause the fabric to become quilted or to otherwise thicken so as to provide additional padding for the wearer. The nitinol used to quilt the fabric could be interspersed within standard fibers of materials such as, but not limited to, polyester, polyimide, polypropylene, PTFE, or the like and would bulk or bunch up the fibers to form the quilt. Such a system would be reuseable and would not require replacement of protective elements, in contrast to using airbags, of which at least the igniters may, most likely, need to be replaced following activation.

The nitinol shape-memory elements may be comprised of nanofabricated or micromachined into the cloth of the garment. Activation of the microscopic nitinol shape-memory elements by applying electricity to the elements, causes them to change shape to stiffen the fabric or cloth of the garment.

Fibers may be extended to project outward from the outer surface of the APG garment. The fibers, like hairs, serve the purpose of creating a slip layer and minimizing shear on the surface of the fabric, thus minimizing abrasion and tears that potentially can damage the person wearing the APG garment. Such fibers may be used in a helmet to enhance head protection. The fibers may be permanently affixed to the helmet or hat or they may be selectively retractable or extendable based on determination of a dangerous condition by a logic controller. Materials suitable for such fibers include, but are not limited to, steel, polyester, polytetrafluoroethylene (PTFE), polyolefin, Kevlar, and the like. The fibers are a suitable enhancement for the protection afforded by the APG collar 70, the APG pants 90, or the APG coat 80. The fiber length ranges from 0.1 inches to 3.0 inches and preferably from 0.25 inches to 1.0 inches. The fiber density is preferably sufficient to visually obscure more than 50% of the surface of the APG garment.

The fibers or hairs on the garment may advantageously be affixed to a layer of material that is separated from the main surface of the garment or helmet. The layer itself may be of low friction material such as PTFE, FEP, or the like, or it may be lubricated in the space between the layer supporting the fibers and the main surface of the garment or helmet using materials such as PTFE, silicone oil, or the like. Relative motion of the fiber-supporting layer is beneficial in deflecting glancing forces directed at the APG or helmet. The fibers or hairs themselves also serve to deflect glancing blows to the garment.

Figure 10:
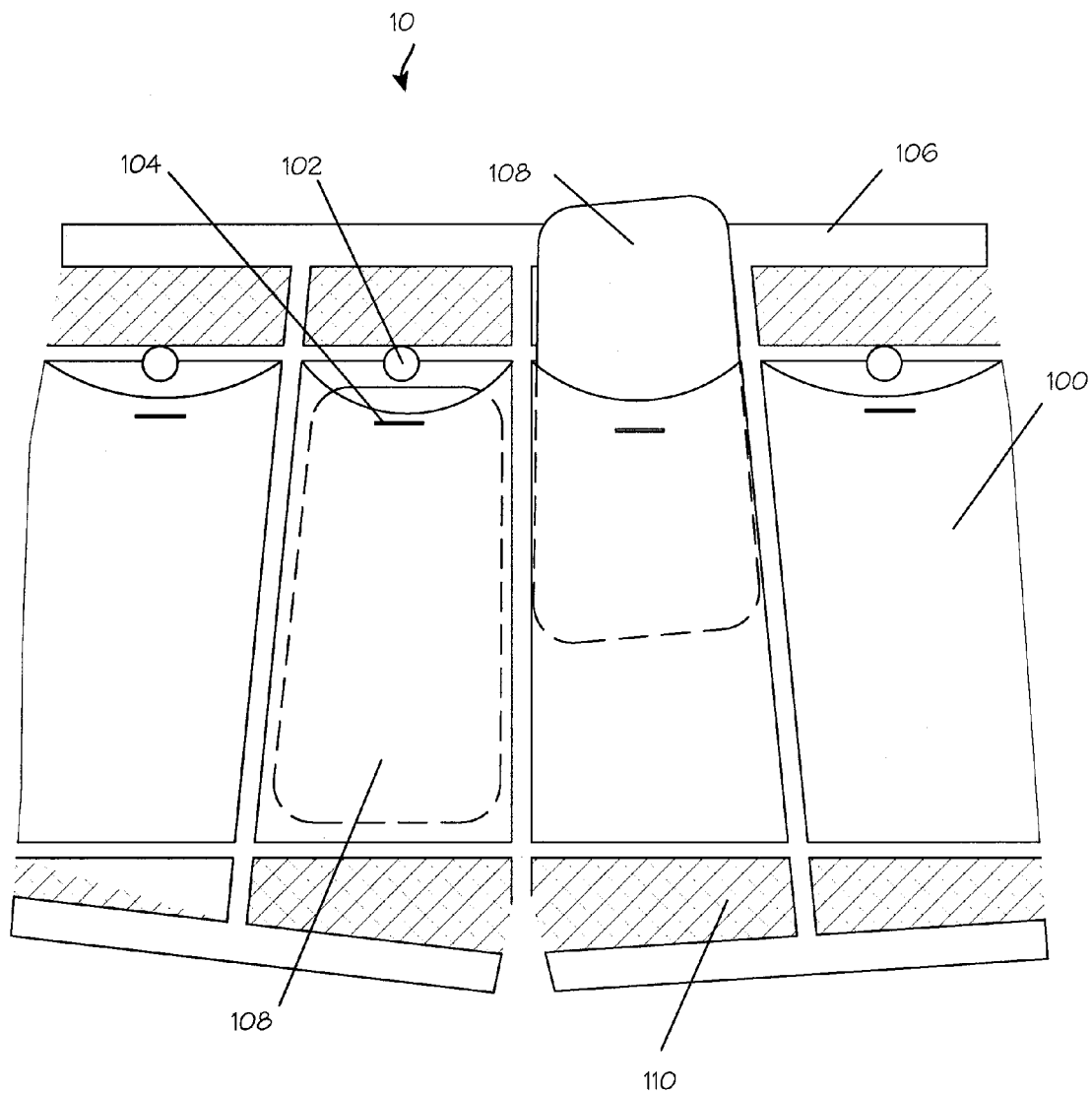
FIG. 10 illustrates a rear view of a pair of APG shorts with pockets into which APG components are inserted.

In FIG. 10, a pair of APG shorts 10 are shown in rear view. The APG shorts 10 further comprise a plurality of pockets 100, a plurality of fasteners 102, a plurality of fastener holes 104, a base garment 106, a plurality of removable isolated APG chambers 108, and a plurality of breathable regions 110.

Referring to FIGS. 3 and 10, the removable isolated APG chambers 108 further comprise one or more accelerometers 14, and/or one or more gyroscopes 16 or rotational accelerometers. The removable isolated APG chambers 108 further comprise a power supply 24, a logic controller 22, a high pressure or compressed gas source 18 and an actuable valve 20 or airbag inflator. The actuable valve 20 or airbag inflator and the accelerometers 14 or gyroscopes 16 are preferably hard wired electrically to the logic controller 22. All components are preferably affixed to the interior surface of the removable isolated APG chambers 108. The logic controller 22 further comprises wireless communication subsystems for short-range communication with other removable isolated APG chambers 108 removably affixed to the base garment 106 by being inserted into the pockets 100, which are integral to the base garment, and secured in place by fasteners 102 and fastener holes 104.

Referring to FIGS. 3 and 10, the wireless communication between the logic controllers 22 on each of the APG chambers 108 is made by methods including, but not limited to, microwave, infrared, ultrasonic, radio waves or similar. The transmissions are preferably digitally encoded to minimize the risk of interference from outside sources. The logic controllers 22 preferably comprise fail-safe mechanisms to activate upon impact but primarily activate upon determination of a fall in progress as evidenced by accelerometer or gyroscope data.

The APG shorts 10 illustrated in FIG. 10 are beneficial because the isolated APG chambers 108 are removable and the base garment 106 is washable. The number of breathable regions 110 is maximized in this configuration to enhance comfort and wearability of the APG shorts 10.

The fasteners 102 and fastener holes 104 comprised in the base garment 106 are illustrative of typical fasteners. Other fasteners suitable for this application include but are not limited to, Velcro, snaps, zippers, and the like.

The APG may comprise three each three-dimensional accelerometers. These accelerometers each read in the X, Y, and Z axis. The three-dimensional accelerometers are located one at the base of the neck, one at or near the right iliac crest and one at or near the left iliac crest. The iliac crest defines a specific location at or about the hip area. The three accelerometers feed nine channels of acceleration data into the onboard logic controller or computer through digital input or analog to digital converters. The logic controller or computer calculates a derivative of the signals over time, specifically by integrating over time, to provide velocity, and takes the integral of the velocity data over time to provide distance. The acceleration, velocity, and distance data are constantly evaluated by a rule-based system that determines whether the measured parameters are within the range of normal safe human motion or whether a fall in progress is occurring and thus triggering activation of a protective device.

The APG can further comprise an optional sonar, proximity, or position sensor to detect proximity to objects and for calibration of the accelerometers. This type of sensor is capable of detection of injurious falls by combining proximity detection (the distance from an object) and closing velocity detection (speed at which an object is being approached). Such a sensor utilizes basic sonar techniques by emitting a set of ultrasonic pulses whose echo is used to perform both measurements. The basic device consists of an ultrasonic transmitter (or transmitters) and a corresponding ultrasonic receiver (or receivers). The basic principle of operation is for the transmitter to periodically emit a set of ultrasonic pulses, which will bounce off of any nearby solid object. These pulses bounce off of nearby solid objects and return to be detected by the receiver. Distance is determined by the time taken for the audio return signal. Velocity is determined by the change in return time (corresponding to a change in distance) between different pulse groups (corresponding to a change in time).

The ultrasonic transmitter should operate in the range between 40 KHz and 70 KHz. This frequency range is roughly the middle of the range used by Bats and is sufficiently above the human hearing range to avoid any negative sensations. High frequency is also more effective at close range measurements and does not propagate as effectively through barriers such as doors and walls (a desirable characteristic).

Simple distance measurement is possible. The velocity of sound is roughly 700 miles per hour or 1027 feet per second. This results in sound traveling 1 foot in approximately 0.97 milliseconds. For a round trip reflection off of a hard surface from a 2-foot distance would be 3.9 milliseconds while from 1 foot would be 1.95 milliseconds. This is well within the range of almost any microprocessor or digital signal processor on the market today.

The approach velocity of concern for falls is in the range of 4 miles per hour or 5.9 feet per second. The final foot of an injurious fall would take approximately 0.17 seconds. There is sufficient time for more than 40 complete echo pulses to be transmitted and received during this period of time. Velocity is calculated by determining the difference between the echo time (distance measurement) of one echo group and the next. For example if echo pulses are emitted at 0.1 seconds apart and the closing distance to an object is 4 miles per hour, the change in the echo time is more than 1 millisecond for each pulse (See Table 1 for the complete closing sequence). Again this is very practical set of times and calculations to perform for any microprocessor or digital signal processor.

TABLE 1

Echo Times for the last second of a 4.0 MPH approach velocity

| Time (sec) | Distance (feet) | Echo (ms) |
| --- | --- | --- |
| 1 | 5.87 | 11.43 |
| 0.9 | 5.28 | 10.29 |
| 0.8 | 4.69 | 9.14 |
| 0.7 | 4.11 | 8.00 |
| 0.6 | 3.52 | 6.86 |
| 0.5 | 2.93 | 5.71 |
| 0.4 | 2.35 | 4.57 |
| 0.3 | 1.76 | 3.43 |
| 0.2 | 1.17 | 2.29 |
| 0.1 | 0.59 | 1.14 |

The time between echo pulse groups can be varied based on distance. When the distance is great, the pulses can be far apart to conserve energy. As the distance gets closer, the echo pulse group rate can be increased to provide increased accuracy for both distance and velocity. This approach is useful in conserving battery power or system energy.

A single frequency/single pulse technique would be very simple but is highly subject to interference. The transmitted ultrasonic signal should be a combination of several short pulses at detectably different frequencies. This technique will prevent any single interference source from disabling the detector. A second significant type of potential interference is objects directly adjacent (such as sitting in a chair, leaning against a wall, etc.). Sonar techniques have a characteristic blind spot preventing the detection of objects very close to the transmitter/receiver. The existence of this characteristic blind spot prevents directly adjacent objects from creating any interference.

The potential for false positives (trigging a pending impact condition at excessive velocity) must be carefully evaluated. Concern has been expressed about the potential of a false trigger when a person walks past a solid object (but does not impact the object). In general if the approach velocity is below the identified injurious velocity, then no potential for a false trigger exists. Efficiency of the sensor is increased when it is determined if normal daily activity creates velocities, which exceed the critical injurious velocity. Initial review of material indicates that there is indeed a gap between normal daily activity velocities and an injurious velocity especially for people in the age and activity group to which these detection devices would apply. Nevertheless, the concept of utilizing multiple dissimilar sensors of which the proximity/velocity sensor is part of a system, which will provide a high degree of reliability while minimizing the potential for being a nuisance to the user.

The digital signal processor, logic controller or computer may comprise software and hardware that allows for a training mode. In this mode, the APG is worn by the patient and the patient goes through a series of defined or undefined movements representing normal daily movement for that individual. This information is used to define parameters of the rule-based system or neural net software that monitors the APG sensors and determines whether or not to activate protective mechanisms. The training mode is generally enabled by a caregiver by generating input code to the computer or by activating a switch which starts training mode. Training mode is activated and deactivated by a manual switch but such switching can be either automatic, timed, or software-driven.

The training mode comprises three basic requirements. First, the manufacturer of the APG predetermines a set of 3 dimensional trajectories and acceleration profiles and programs those into the APG. These acceleration profiles represent several common composite 3 dimensional motions that can be classified by acceleration, velocity, rotation, distance or sequence as a falling condition for a majority of people. By way of example, the manufacturer may preset a set of acceleration profiles defining, for example, a) slipping or; b) tripping forward. The APG is then sold or leased to a user, containing the preset profiles for categorical fall motions. The user can then elect to input his, or her, own particular or individual set of acceleration profiles. The user identifies to the APG that the input activities define "normal" or "routine" activities for the particular user. They are "normal" or "routine" for the user in that they do not represent activities where the user is actually falling. If any of these user set profiles coincide with any of the manufacturer-preset profiles for categorical falls, the user removes the preset activity as a condition for deployment of the gas source. As a result, the user can engage in any routine activity, e.g. vigorous calisthenics, without danger of deployment of the APG.

The sensors can be calibrated with respect to a pre-assigned baseline. This calibration is either done with the aforementioned training mode, or by use of other transducers or external reference points. A patient may be fitted with the APG and a caregiver uses external instrumentation to measure the exact locations of the sensors or implants that guide location of the sensors. A sonar or position device may be used to determine the position of each transducer (accelerometer, other position sensor, rotational sensors, etc.) or certain reference points on the patient.

The APG system may provide a self-test function to ensure that all systems are within normal operating parameters. This self-test can be manually activated, automatically activated, or activated on a timed basis, once a day, for example. The APG system, further comprises on-off switching to disable the system as desired. This on-off function can be set so that only a caregiver can operate it or it can be set that the patient can also operate the on-off function.

In order to reduce the number of false positives, the logic controller may be programmed with predetermined rules that define the motion signatures for the major activity states as well as the transitions between those states. Other rules define the significant departures from the normal motions that indicate falls.

The accelerometers or sensors may be taped to the body, implanted subcutaneously or intramuscularly or mounted on a specially designed garment. Power is transmitted to the sensors transcutaneously through coils or through RF ID type systems with antennas distributed within at least a portion of the active protective garment. The computer and power supply are external and part of the garment. Implanted or surface-mounted devices serve as positioning clips or locating devices to ensure placement of the sensors at the correct location on the body. Such implanted devices may comprise magnets, or, or electronically communicating RF ID device. Surface-mounted markings include tattoos, scars, and the like.

The motion sensors, consisting of the gyroscopes, magnetometers, gravity sensors and accelerometers, linear or rotational but especially linear, are, in a preferred embodiment, separated by distance sufficient to generate relative motions. The accelerometers should be spaced to generate data from different parts of the body, particularly the upper and lower torso. The spacing of the accelerometers may be one on the left iliac crest, one on the right iliac crest, and one at or near the base of the neck. Other configurations are also appropriate, so long as the sensors are placed at some distance apart from each other so that they are able to discriminate the rotational data readings from each motion sensor. For example other regions at or about the hip may be suitable as substitutes for the iliac crest. Three each three-dimensional accelerometers spaced in this configuration can translate in three axes at their locations as well as rotation about all three major axes. The accelerometers can be placed on a part of the body where the relative positions remain relatively constant so that rotational accelerations, rotational velocities and distances can be calculated with minimal errors caused by changes in spacing. The sensor location is optimized so that conjugate and disconjugate motions of the body can be distinguished.

The system may comprise one or more algorithms, implemented through software, firmware, or hardware. An exemplary algorithm for a typical slipping fall backward will trigger activation of the device if the following conditions are met:

1. Both hip accelerometers receive initially little downward acceleration (normal status);
2. The neck accelerometer accelerates posteriorly in the anterior-posterior plane of the patient while the hip accelerometers accelerate, simultaneously with the neck accelerometer, anteriorly or not at all;
3. The hip accelerometers begin accelerating toward the ground or in a direction toward the feet with some posterior component with composite vertical velocities (calculated by taking a derivative function of acceleration over time, specifically by integration) reaching greater than 1 meter per second;

4. The neck accelerometer continues to measure accelerations in the posterior direction with integrated overall velocities exceeding 1 meter per second;
5. The activation of the triggering mechanism for the airbag will preferably occur once velocities exceed 1 meter per second, although other abnormal motion sequences may trigger deployment of protective measures at velocities well below this threshold.
6. As aggregate or composite velocities approach 2 meters per second, an impact is imminent.

Another exemplary categorical fall algorithm for a typical tripping fall forward is:
1. both hip accelerometers receive initially little downward acceleration (normal status);
2. the base of neck accelerometer suddenly accelerates anteriorly in the anterior-posterior plane of the wearer while the hip accelerometers accelerate, simultaneously with the neck accelerometer, only slightly anteriorly or not at all;
3. the neck accelerometer continues to accelerate and reaches the derivative integrated velocities in excess of 1 meter per second at which point triggering of the protection device is activated;
4. the pelvic accelerometers provide similar anterior acceleration measurements indicative of high velocity, anterior and downward rotation and imminent fall.

As another example, should composite velocities exceeding negative 1 meter per second occur without the relative rotation of the neck relative to the hips, activation of the protection mechanism would not be warranted. Such a condition could occur only in a car or other moving vehicle, jumping off a substantial height, etc.

The APG shorts 10 may include a GPS system and a transmitter suitable for communications with cell phone systems to notify other people or emergency people that a fall has occurred and the APG shorts were activated. Inter-APG signals may be transmitted via wires or by wireless methods. The Active Protective Garment may be a coat, pants, shirt, vest, helmet, or other type of clothing. The system may be designed to protect the wearer from a fall from standing, from bed, from being thrown off a motorcycle or bicycle, or it may protect the wearer from falling a substantial distance such as 10 to 30 feet.

The system may include one more multifunction motion sensor arrays and data fusion algorithms in the motion sensors or control system. The sensors may comprise three axis accelerometers, inertial measurement units and gyroscopes, angular velocity sensors, magnetic field sensors and gravitational sensors. The control system can recognize composite, sequential, three-dimensional movements. Preferably, two multifunction motion sensor arrays would be used in the APG system. Sampling rates for the entire system will generally fall in the range of 10 to 100,000 samples per second and preferably between 100 and 10,000 samples per second. Suitable sensors include Model MT9 inertial measurement units available from Xsens.

A magnetometer (compass type device), gyroscope (inertial measurement unit), or gravity sensor (level type device) are beneficial in making the necessary measurements. A magnetometer can update its position using today's technology at a rate of around 100 samples per second, which would be sufficient for use on the APG. The magnetometer is the ideal way to calibrate the system's orientation relative to, say, magnetic north, etc. It could also serve as the primary measurement device for motions such as pelvic rotation.

The programming of the logic circuitry to remember and subsequently recognize the sequences of three dimensional motions of the upper and lower torso that characterize normal walking, sitting down, assuming recumbency, rising from the sitting position, stooping to pick up an object and other activities of daily living is a beneficial feature of the system. The activities of daily living and the motions of accidental falls can be recognized and reliably distinguished from each other by the integrated outputs of two or more multifunction motion sensors located on the human torso. In this construction, the torso may be represented as a box or other geometric solid that may further be tracked through space and time. In an embodiment, the box or geometric solid representing the torso may comprise flexing elements to simulate bending of the spine. The actions of the upper and lower portions of the geometric solid, representing the torso, may tracked independently to follow flexion or extension. The separate sensors are important in tracking the motion of the two portions of the torso, previously discussed. This plurality of sensors is important in discrimination of a fall in progress from a motion of daily living such as stooping over to pick up an object from the floor. The reduction of the torso to a geometric solid is beneficial in simplifying the model for analysis by computational means.

The logic circuitry is advantageously programmed with rules that distinguish normal motions from fall-associated motions by the observed accelerations, velocities, directions, rotations and distances of motion of the upper and lower torso sensors and by the actual sequence in which composite motions occur. The operative rules will be derived from observed normal activities of the individual and stereotypical human behaviors such as the act of sitting down. Other rules will refer to the hallmarks of categorical fall motions based on accelerations, velocities, directions of motion, rotations and distances or sequences of motion that do not occur during normal activities and that indicate the loss of balance and the presence of an accidental fall. An example of such a rule includes the rapid posterior or postero-lateral and downward movement of the upper thorax as the pelvis moves downward. Such a combination of motions represents a categorical fall.

An alternative version of the system can, perform frequent, automatic re-calibration of the height of the sensors above the ground by rules referring to the particular activity in which the monitored subject is engaged. For example, when the logic circuit recognizes the motions of standing up or walking, it can be automatically and continuously recalibrated to know that the pelvis-level sensor is at a height above the ground that was measured and programmed into the logic circuit, with the subject standing, at the time the sensor is first worn or implanted. The thoracic sensor can also be known by the logic circuit to be vertically above the pelvic sensor by a measured and previously programmed or inputted distance. The logic circuitry is able to recalibrate the position and orientation of two or more of the motion sensors on or in the torso relative to various landmarks. These landmarks include: the height of each sensor above the ground or floor, the spatial relationship of each sensor with respect to the other sensors, the relationship of each sensor to the earth's gravitational force, the relationship of each sensor to the earths magnetic field, and the relationship of each sensor to the anterior-posterior axis of the body by reference to rules based on observed body motions. Distance recalibration can be accomplished using sonar or distance measuring devices, gravitation orientation can be made using gravity sensors or other gravity measuring devices such as levels, and magnetic field orientation can be determined using magnetometers. The system can comprise low-pressure airbags that expand to less than twice atmospheric pressure when fully deployed. Airbags so configured can assume the desired shape upon inflation without becoming hard or unyielding on impact with a surface or object. The airbags do not necessarily need to be fabricated from fluid or gas impermeable membranes. Airbags that are fabricated from porous materials may inflate under rapid pressurization by the airbag inflator and then deflate once their function of impact protection or force redistribution is completed. The airbags may advantageously be molded or contoured and curve around the body surface, according to their molded shape when deployed. These airbags tend to form three-dimensional geometries that vary from standard flat planar geometries. The airbags may further be contoured to fit specific sites such as, but not limited to, the head, neck, torso, hips and pelvis. For example, an airbag configured for the cervical spine can be about two inches thick upon inflation and around three to four inches in vertical dimension. The configuration is circular or substantially circumferential. Non-circumferential head airbags can project 10 to 12 inches upward from the base of the neck so that the top of the airbag expands above the level of the crown of the head. The airbags may also be advantageously sized for different individuals. The airbags may, in this embodiment, be either custom sized or a range of predetermined sizes, for example, small, medium, and large, may be provided. Separate airbags can be provided for the neck, head torso, and hips.

The user sensors may also be recalibrated based on the activity or position of the user's body, without reference to any external standard. New programs can be triggered within the logic controller based upon the state of the monitored user or on the observation of a transition between states. Observed torso motions can be referenced to the body state or transition as being normal or abnormal. Parameters are programmed for allowable motions in each direction for each body state and transition. This is performed either by a neutral network or a statistical program of pattern matching. The range of normal trajectories during each of the transitions is established. Downward motions of the torso not corresponding to programmed parameters for a given transition because of an abnormal sequence, acceleration or trajectory are recognized as falls. The delineation of the normal motion signatures for the standing/walking state, the seated state and the recumbent state for the transitions between states is programmed during a training phase.

The airbags may deploy by projecting from soft, breathable, protective pods located on or in the collar, vertical straps, struts, belts or harness, for example. The hip pods would open fully at the bottom, like a clamshell opening, to permit egress of the inflating airbag, in contrast to a holster, for example, which is functionally closed at the bottom. Pods configured for holding hip airbags would, in an embodiment, advantageously not be attached to the hip or thigh by a strap, or garment, in contrast to the configuration of a holster. The pods, in an embodiment, may open distally and laterally to allow access for changing airbag assemblies and to permit egress for airbags being deployed from the pods. The pods may have soft, molded plastic hoops at their edges to keep their shape and maintain their position on the body. The pods can be constructed so that the packaged airbag assembly can only be inserted correctly. Orientation of the airbag relative to the pod is maintained by labeling, geometries that only line up one way, providing orientation markers or features, and the like. Velcro strips can be provided on the airbag package and within pods, preferably color-coded, for both the size and intended anatomic location of the airbag. For example, a green color might indicate the left hip, large bag. A blue airbag would be designated for the head. Red would designate a right rib airbag of small size, etc.

Figure 11A:
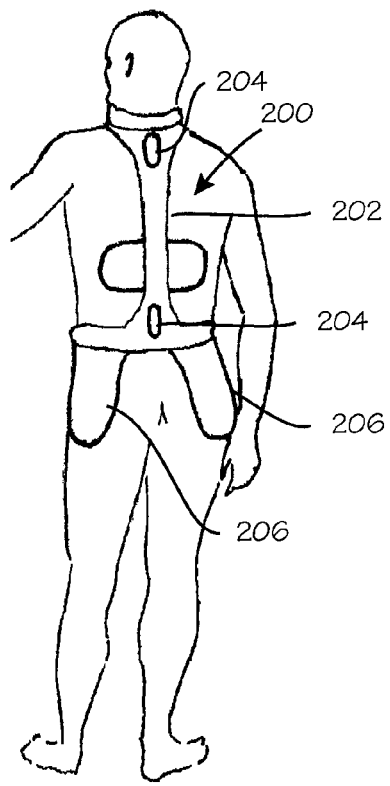
FIG. 11A illustrates a rear view of a person wearing a harness.

FIG. 11A shows a harness 200, which facilitates integration of the entire system. The harness 200 is useful for protection of the head, cervical spine, the ribs and the hips of elderly fall victims. The harness 200 comprises a vertical spinal support 202, a plurality of sensor arrays 204, a plurality of airbags or pods for holding airbags 206, an attachment device (not shown), logic circuitry (not shown), and the power supply (not shown). The vertical spinal support comprises a stay secured to the garment such that it is vertically oriented relative to the patient, and extends from the lower torso or pelvic brim to the upper torso or neck of the patient when the garment is worn. The harness 200 could ideally be a stand-alone garment to be layered under or between other garments or basic harness elements could be built into a vest, shirt, coat, skirt, dress, nightgown, or other clothing item. The harness 200 appears as an open vest that is separated at the front and can be closed at the front using attachment devices such as, but not limited to, a zipper, button, grips, Velcro, etc. Molded plastic hoops can maintain relative position of the aforementioned pods and the harness. The pods 206 may reversibly attach to the harness using hook and loop fasteners, snaps, buttons, or the like. The structure of the harness is such that the vertical spinal support 202 can flex but not foreshorten or lengthen so that distance between sensors 204 is substantially fixed. Airbags or pods 206 containing airbags are located, for example, at the hips, in the middle of the back for rib protection, and in a Nehru-type collar for neck, cervical spine, and head protection.

Figure 11B:
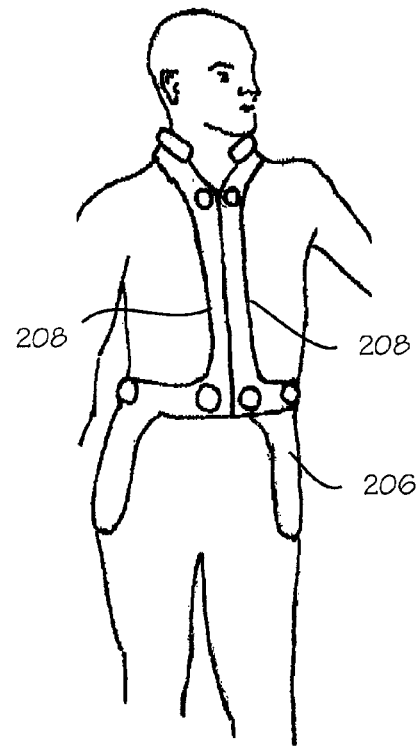
FIG. 11B illustrates a front view of a person wearing a harness.
Figure 11C:
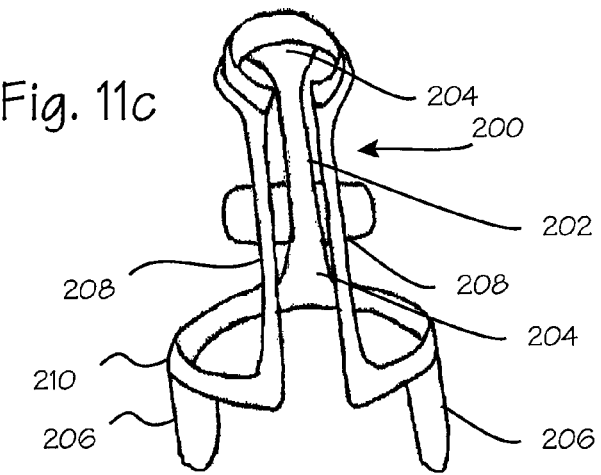
FIG. 11C illustrates a front view of the harness without the wearer.
Figure 12:
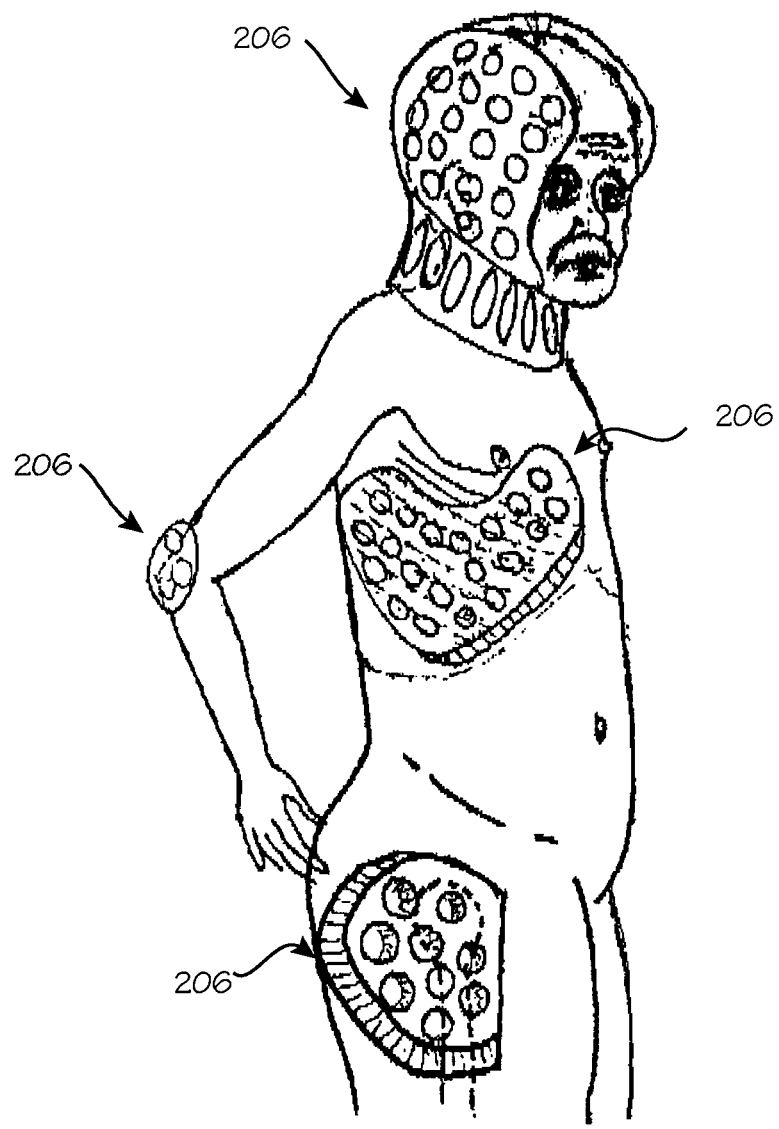
FIG. 12 illustrates a person with a series of deployed anatomically shaped airbags

FIGS. 11B and 11C illustrates the harness 200 showing the vertical spinal support 202, a collar pod 206, a rib pod 206, and two hip pods 206, front plackets 208, and the waist strap 210. The device may be embodied in an open harness as shown, or a full shirt or vest, with the stiff, fixed length vertical spinal support secured to the vest. The sensors 204 could be sited anywhere along the vest or harness 200, but the preferred location for the sensors is in or near the midline of the upper thorax and the pelvic brim. The logic circuitry and power supply can be located anywhere on the structure of the harness 200, but most likely at or near the waistband of the harness. The harness may be used to support airbags and/or airbag pods a various vulnerable areas of the body, as shown in FIG. 12, which illustrates airbags 206 covering the lateral hip area, the lower rigs, the neck and head, and the elbow.

The sensors may communicate wirelessly, using means described elsewhere in this disclosure, with the logic circuitry or the communication bus may be hard wired within straps of the harness. Alternatively, the communication may use a combination of hard-wired and wireless methodology. The logic circuitry can communicate with the gas generator, whether pyrotechnic or a gas canister and valve, using wireless or wired technology. Airbags for rib, cervical vertebrae, or other protection device can deploy from pods or straps on the harness. Alternatively, a rib airbag assembly may be attached to the patient or the harness directly by straps. The vertical posterior or anterior strut of the harness containing two or more motion sensors would have one sensor at the level of the upper thorax and one at the level of the pelvic brim, at about the level of the fifth lumbar vertebra. In another embodiment, the system comprises a sensor array in which multiple data-fused outputs are transmitted to the logic circuitry by wired or wireless connection means. A posterior or anterior strut of the body harness can be configured to maintain the vertical alignment of two sensors and maintains a fixed inter-sensor distance. Maintaining a fixed inter-sensor distance is important to minimizing errors in the data algorithms. The harness can further comprise a vertical posterior strut containing closed or open cell foam or other padding elements in which sensors, gas generators, batteries, and electronics may be embedded in the foam for concealment and protection. The harness would preferably be offered in various sizes to accommodate persons of different height, proportion, and body mass. The harness may further be adjustable to fit a variety of size persons over all or part of the range of human shapes and sizes. The harness can further have a hook and loop, such as Velcro, or other attachment points for pods, deflated airbags, gas generators, electronics, and other system components. The belt and straps of a harness system may comprise elastic materials to maintain the harness comfortably close to the body and to facilitate donning and removal of the APG. The structure of the harness will further be water resistant and resistant to stains by way of chemical treatments to the fibers using chemicals such as ScotchGuard, etc.

The pods may advantageously have a hook and loop fastener such as Velcro, allowing easy and quick attachment of vacuum-packed airbag assemblies with similar strips on their surface allowing for secure fastening to the pod. The pods may further be fabricated from breathable fabrics such, but not limited to, as Gore Tex, cotton, loose weaves of polyester, and the like.

The airbags can be configured to curve upon deployment. This is accomplished mainly by their molded shape but is assisted by the resistance provided by the inner surfaces of any common garments worn over the plane of the deploying airbag. By this arrangement, it is possible to protect the hips and pelvis, whether the hip is flexed or extended during a fall, despite the absence of any fixed attachment of pod to the surface of the thigh or hip. One exemplary way of fabricating a curving airbag is to provide a segmented and sequentially expanded structure. Each segment inflates and forms the basis of the next segment. Using such a segmented or curved airbag, an anatomical body part such as the head, neck, or hip might be completely surrounded by an airbag that deploys from a pod that otherwise does not surround the body part. In another embodiment, separate airbags are separately and sequentially activated, the deployment of which is controlled by the logic circuitry to determine and control the timing, force, and speed of inflation of each airbag. The airbags may further comprise integral hoops or other structural elements, such as sail-type battens, to facilitate achievement of ideal shape during deployment. The airbags may comprise reinforcing bars or struts integrated into the outer surface fabric. The bars may be fabricated from thin pieces of high strength materials such as, but not limited to, polyester, polyimide, and the like.

Another feature of the system is to seal the airbag, along with its triggering mechanism, inflator, or both, within a vacuum pack to minimize the size of the structure. In this embodiment, the use of talc or other material to prevent sticking of the airbag surfaces to each other is beneficial. To further minimize the bulk of the system, the gas canisters or pyrotechnic airbag inflators may be flattened or contour-shaped to minimize the thickness of the airbag-generator assembly and increase wearability of the device. The airbags, batteries, gas generator, etc. may be packaged, together or separately, in a hermetically or otherwise sealed container, which is waterproof and resistant to contamination from the environment. The airbag is preferably vacuum-packed in such a way that the vacuum pack can easily burst or open upon deployment of the airbag.

With regard to detecting and monitoring the motion of the torso, one embodiment is to place sensors in or on the torso, at least one sensor above and at least one sensor below the level of the umbilicus at or near the mid-line of the torso. In this configuration, the system can monitor the motion of the torso as two separate units comprising an upper and a lower part. The logic circuitry can be programmed to always know where the anterior surface of the body is located, the anterior surface being defined as the plane generally including the abdomen and chest of the wearer.

The logic circuit is capable of distinguishing, by integration of data from two or more torso sensors with data-fusion algorithms, information such as: the motion of walking with a gait that is normal or abnormal for the individual, the composite three-dimensional sequence of motions for sitting down, the composite three dimensional motion pattern for assuming recumbency, and the composite three dimensional motion pattern for standing up from sitting. The logic circuit can further determine the composite three dimensional motion pattern for getting into a car, the composite three dimensional pattern for ascending or descending one step or a flight of steps, and the composite three dimensional motion pattern for picking up an object from the floor. The system can also distinguish categorical fall motions by evaluation of torso velocity, acceleration, direction, time, distance, rotation, sensor distance above the floor, sequence of motions, as well as by reference to pre-programmed rules that describe categorical fall motion. The logic circuitry can be governed by rules that are based on stereotypical human behavior. An example of a normal human motion is that the posterior descent of the pelvis, will be preceded by a slow rotation of the torso and by anterior and downward motion of the upper thorax if a patient is sitting but not falling. An example of a rule describing fall motion is that the upper thorax will never move rapidly posterior or posterio-laterally and downward while the pelvis is moving downward unless the subject is falling.

The motion sensors can be externally powered by wired bus, RF-ID, etc., or they can be internally powered by batteries, capacitors, or the like. The motion sensors can further comprise minor or major components of the logic circuitry. By providing the motion sensors with some or all of the logic circuitry, it is possible to add redundancy and the benefits of distributed processing to the system.

The logic circuitry is capable of triggering an audible or skin-vibrating signal to the wearer, for example a vibrator mounted in the soles of one or more shoes, of the device if an abnormal gait is recognized by the logic circuit. The logic circuitry is capable of triggering a call to emergency medical services (EMS) if a fall is observed and the patient fails to fulfill the algorithm for rising to a standing or sitting position, or if the wearer fails to activate an OK signal on the system.

In yet another embodiment, the logic circuitry is capable of triggering deployment of protective devices separately mounted on the floor, a stairwell, a walker, cane, wheelchair, furniture, and the like. Such triggering can be accomplished using wireless technologies such as ultrasound, or some part of the electromagnetic spectrum. A walker can be configured to comprise airbags to cushion the fall of a user should a fall be detected on the part of the user or the walker by means of walker-mounted sensors. The walker can further be configured with a gyroscopic device to help maintain vertical stability in the event that an attempt is made to pull the walker over. The gyroscope can be used as a sensor or as a primary force-leveling device.

The collar of the APG can deploy airbags to protect the neck, the cervical spine, and the head. This can be done using an inner airbag that is approximately between two and 8 inches high and preferably between 3 and 5 inches high. This airbag can inflate to protect the cervical spine by providing a support collar against torsion loads and to prevent compression stresses on the neck because the head and chin are supported against the shoulders of the wearer. An outer airbag or set of airbags protects the head and serves to reinforce the inner airbag. These outer airbags can also be fabricated as part of the inner airbag so that separate airbags are not used. The airbags are preferably sized and shaped to serve the intended function. By sequentially inflating a series of airbags, it is possible to generate three-dimensional geometries more easily and for a full helmet to deploy that no only protects the side of the head but also the top of the head.

Most common rib fractures in the elderly involve ribs number seven eight and nine. It is important to protect these ribs as they are not well protected by the scapula, breast or arm. An airbag designed for the ribs can be attached by Velcro or other attachment in or on a shirt or undershirt, or built into a pod or a harness. The Velcro strip or other fastener pre-attached to a garment would provide for ease of positioning at the correct location.

In another embodiment, the system can use sensors and logic circuitry that recognize fall patterns and decide what part of the person, for example the head, will strike an object and require protection. The system can deploy airbags selectively to protect only those body parts requiring protection, thus minimizing the need to replace or recharge unnecessarily deployed airbags.

It is a desirable feature of the present invention that the microprocessor will "know" the relative position of the thoracic and pelvic sensors. These relative positions may be known by reference to an external reference point, but preferably, the microprocessor will re-calibrate the vertical relationship of the thoracic and pelvic sensors each time the patient assumes a sitting position or shows the motion of walking. Under these two circumstances, the microprocessor will be re-calibrated to recognize the position of the upper thoracic sensor as being vertically straight above the pelvic sensor at a distance programmed at the time of sensor placement or implantation.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A motion analysis system comprising:
    at least one orientation sensor configured to detect three-dimensional torso motion over time, the at least one orientation sensor comprising:
        a multiaxial accelerometer configured to detect acceleration in at least three orthogonal directions, and
        a gyroscope; and
    a controller configured to receive data from the at least one orientation sensor, the controller programmed to process the data to:
        determine at least one of a state and a transition of the torso;
        identify normal parameters for the determined at least one of the state and transition; and
        determine whether motion of the torso is outside the normal parameters
    wherein the controller is configured to identify, in real-time, the occurrence of a fall in progress of an individual from at least one of a standing state, a standing-to-seated transition, and a seated-to-standing transition.

2. The motion analysis system of claim 1, wherein the at least one orientation sensor is further configured to detect pitch, roll, and yaw of the torso.

3. The motion analysis system of claim 1, wherein the at least one orientation sensor is further configured to detect an acceleration of each of pitch, roll, and yaw of the torso, and a vertical acceleration of the torso referenced to gravity.

4. The motion analysis system of claim 1, wherein the at least one orientation sensor is further configured to detect a velocity of each of pitch, roll, and yaw of the torso, and a vertical velocity of the torso.

5. The motion analysis system of claim 1, wherein the at least one orientation sensor is further configured to detect a total acceleration of the torso.

6. The motion analysis system of claim 1, wherein the at least one orientation sensor is further configured to detect a trajectory of the torso.

7. The motion analysis system of claim 1, wherein the at least one orientation sensor comprises an inertial measurement unit.

8. The motion analysis system of claim 1, wherein the at least one orientation sensor further comprises a magnetic field sensor.

9. The motion analysis system of claim 1, wherein the state of the torso comprises at least one of standing, walking, seated, and recumbent.

10. The motion analysis system of claim 1, wherein the transition of the torso comprises at least one of standing-to-seated, seated-to-standing, seated-to-recumbent, and recumbent-to-seated.

11. The motion analysis system of claim 1, wherein the controller is programmed to determine the state of the torso based on a gravity-referenced motion intrinsic to the state, the orientation of the at least one sensor, and a transition of the torso that led to the state.

12. The motion analysis system of claim 1, wherein the controller is programmed to determine the transition of the torso based on a state from which the transition originates and the three-dimensional torso motion referenced to gravity.

13. The motion analysis system of claim 1, wherein:
    the controller is programmed to identify normal parameters for the state by reference to parameters for normal states that are programmed into the controller, the parameters for normal states being based on experimental, orientation-sensor monitoring of the torso motions of individuals who are standing, walking, seated, and recumbent.

14. The motion analysis system of claim 13, wherein the controller is programmed to identify normal parameters for the transition by reference to parameters for normal transitions that are programmed into the controller, the parameters for normal transitions being based on experimental, orientation-sensor monitoring of the torso motions of individuals who are transitioning between standing and sitting, sitting and standing, sitting and lying down, and lying down and standing.

15. The motion analysis system of claim 13, wherein the parameters for normal states or normal transitions are parameters developed by observation of a user of the motion analysis system.

16. The motion analysis system of claim 15, wherein the observation of the user of the motion analysis system is performed during a training mode.

17. The motion analysis system of claim 1, wherein the parameters include an attitude of the torso, a three-dimensional trajectory of the torso referenced to gravity, a duration of a nearly weightless state of the torso, and angular rates of the torso along multiple axis during descent of the torso.

18. The motion analysis system of claim 17, wherein the parameters further include a sequence of motions and total acceleration, including a gravitational reference, and the force and duration of deceleration.

19. The motion analysis system of claim 18, wherein the controller is further configured to determine whether a force and duration of deceleration of the torso are outside normal parameters for a force and duration of deceleration.

20. The motion analysis system of claim 1, wherein the controller is further configured to determine that a descending motion of the torso, referenced to gravity, that is greater than one standard deviation beyond one or more of the normal parameters is a fall of an individual.

21. The motion analysis system of claim 1, wherein the controller is configured to determine whether the motion of the torso is outside the normal parameters based on data obtained from the at least one orientation sensor during a period of between 1 second and 10 minutes.

22. The motion analysis system of claim 1, wherein the normal parameters are set such that motion of the torso that is outside the normal parameters is indicative of a fall.

23. The motion analysis system of claim 1, further comprising at least one additional gyroscope.

24. The motion analysis system of claim 1, wherein the multiaxial accelerometer and the gyroscope are hard wired to the controller.

25. The motion analysis system of claim 1, wherein the at least one orientation sensor is configured for wireless communication with the controller.

26. The motion analysis system of claim 1,
wherein the controller is configured to identify the standing-to-seated transition based at least on (i) a magnitude of an anterior or anterolateral tilt of the torso detected by the at least one orientation sensor, and (ii) a posterior descent of the pelvis measured by the at least one orientation sensor,
wherein the controller is configured to identify the seated-to-standing transition based at least on (i) a magnitude of an anterior or anterolateral tilt of the torso detected by the at least one orientation sensor, and (ii) an anterior ascent of the torso measured by the at least one orientation sensor,
wherein the controller is configured to identify, in real-time, the occurrence of the fall in progress of the individual from a standing state, the standing-to-seated transition, or the seated-to-standing transition, based on at least one of (i) a lateral and downward acceleration exceeding a predetermined threshold, (ii) a cephalad acceleration exceeding a predetermined threshold, and (iii) a backward and downward motion without prior transitional movement of a forward tilt within a predetermined angle range.

27. The motion analysis system of claim 1, wherein the controller is configured to identify a normal standing-to-seated transition based on statistical conformity within programmed limits with (i) a magnitude and direction of three-dimensional torso tilt, (ii) a three-dimensional trajectory of the torso, (iii) angular rates of the torso in X, Y and Z axes, and (iv) a duration of a nearly-weightless state of the torso.

28. The motion analysis system of claim 1, wherein the controller is configured to identify the seated-to-standing transition based on statistical conformity within programmed limits with (i) a magnitude and direction of three-dimensional torso tilt, (ii) a three-dimensional trajectory of the torso, (iii) angular rates of the torso in the X, Y and Z axes, and (iv) an upward acceleration of the torso opposed to gravity.

29. The motion analysis system of claim 1, wherein the controller is configured to identify, in real-time, the occurrence of a fall-in-progress from the standing state, the standing-to-seated transition or the seated-standing transition based on deviations beyond threshold values from at least one of (i) three-dimensional torso tilt, (ii) three-dimensional torso trajectory, (iii) angular rates of the torso in the X, Y and Z axes, and (iv) a duration of a nearly-weightless state of the torso.

30. A motion analysis system comprising:
at least one orientation sensor configured to detect three-dimensional torso motion over time, the at least one orientation sensor comprising:
a multiaxial accelerometer configured to detect acceleration in at least three orthogonal directions, and
a gyroscope; and
a controller configured to receive data from the at least one orientation sensor, the controller programmed to process the data to identify, in real-time, the occurrence of a fall in progress of an individual from at least one of a standing state, a standing-to-seated transition, and a seated-to-standing transition.

\* \* \* \* \*